US009163057B2

(12) United States Patent
Belardinelli et al.

(10) Patent No.: US 9,163,057 B2
(45) Date of Patent: *Oct. 20, 2015

(54) METHODS OF MYOCARDIAL PERFUSION IMAGING

(71) Applicant: Gilead Sciences, Inc., Foster City, CA (US)

(72) Inventors: Luiz Belardinelli, Palo Alto, CA (US); Brent K. Blackburn, Los Altos, CA (US); Zhenhai Gao, San Jose, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/014,169

(22) Filed: Aug. 29, 2013

(65) Prior Publication Data

US 2015/0023867 A1  Jan. 22, 2015

Related U.S. Application Data

(63) Continuation of application No. 13/525,223, filed on Jun. 15, 2012, now Pat. No. 8,536,150, which is a continuation of application No. 13/286,069, filed on Oct. 31, 2011, now abandoned, which is a continuation of application No. 12/435,176, filed on May 4, 2009, now Pat. No. 8,071,566, which is a continuation of application No. 11/070,768, filed on Mar. 2, 2005, now Pat. No. 7,582,617, which is a continuation of application No. 10/614,702, filed on Mar. 7, 2003, now abandoned, which is a continuation of application No. 09/792,617, filed on Feb. 23, 2001, now abandoned.

(60) Provisional application No. 60/219,876, filed on Jul. 21, 2000, provisional application No. 60/184,296, filed on Feb. 23, 2000.

(51) Int. Cl.
*A01N 43/04* (2006.01)
*A61K 31/70* (2006.01)
*A61K 51/00* (2006.01)
*A61M 36/14* (2006.01)
*C07H 19/16* (2006.01)
*G01N 33/50* (2006.01)
*G01N 33/566* (2006.01)

(52) U.S. Cl.
CPC ............... *C07H 19/16* (2013.01); *A61K 51/00* (2013.01); *G01N 33/502* (2013.01); *G01N 33/5008* (2013.01); *G01N 33/5082* (2013.01); *G01N 33/5088* (2013.01); *G01N 33/566* (2013.01); *G01N 2500/04* (2013.01)

(58) Field of Classification Search
CPC ............ G01N 33/5008; G01N 33/502; G01N 33/5082; G01N 33/566; G01N 33/5088; G01N 2500/00; A61K 51/00; C07H 19/16
See application file for complete search history.

(56) References Cited

U.S. PATENT DOCUMENTS

| 3,845,770 | A | 11/1974 | Theeuwes et al. |
| 4,089,959 | A | 5/1978 | Diamond |
| 4,120,947 | A | 10/1978 | Diamond |
| 4,325,956 | A | 4/1982 | Kjellin et al. |
| 4,326,525 | A | 4/1982 | Swanson et al. |
| 4,593,095 | A | 6/1986 | Snyder et al. |
| 4,696,932 | A | 9/1987 | Jacobson et al. |
| 4,804,664 | A | 2/1989 | Kjellin et al. |
| 4,902,514 | A | 2/1990 | Barclay et al. |
| 4,956,345 | A | 9/1990 | Miyasaka et al. |
| 4,968,697 | A | 11/1990 | Hutchison |
| 4,992,445 | A | 2/1991 | Lawter et al. |
| 5,001,139 | A | 3/1991 | Lawter et al. |
| 5,032,252 | A | 7/1991 | Owen et al. |
| 5,070,877 | A | 12/1991 | Mohiuddin et al. |
| 5,189,027 | A | 2/1993 | Miyashita et al. |
| 5,270,304 | A | 12/1993 | Kogi et al. |
| 5,459,254 | A | 10/1995 | Yamaguchi et al. |
| 5,516,894 | A | 5/1996 | Reppert |
| 5,593,975 | A | 1/1997 | Cristalli |
| 5,616,345 | A | 4/1997 | Geoghegan et al. |
| 5,641,784 | A | 6/1997 | Kufner-Muhl et al. |
| 5,646,156 | A | 7/1997 | Jacobsen et al. |
| 5,670,498 | A | 9/1997 | Suzuki et al. |
| 5,703,085 | A | 12/1997 | Suzuki et al. |
| 5,704,491 | A | 1/1998 | Graves |
| 5,705,491 | A | 1/1998 | Yamada |
| 5,770,716 | A | 6/1998 | Khan et al. |
| 5,776,960 | A | 7/1998 | Oppong et al. |
| 5,780,481 | A | 7/1998 | Jacobson et al. |

(Continued)

FOREIGN PATENT DOCUMENTS

| CA | 965411 | 4/1975 |
| CA | 2064742 | 12/1991 |

(Continued)

OTHER PUBLICATIONS

Martinson et al., "Potent Adenosine Receptor Antagonists that are Selective for the A1 Receptor Subtype," Molecular Pharmacology, 31 (3), 247-252 (Mar. 1986).*

Bergmann et al., "Oxidation of Hypoxanthines, Bearing 8-Aryl or 8-Pyridyl Substituents, by Bovine Milk Xanthine Oxidase,", Biochimica et Biophysica Acta, vol. 484, No. 2, pp. 275-289 (1977).

Birdsall et al., "Purine N-Oxides-XL The 3-Acyloxypurine 8-Substitution Reaction: Scope: Syntheses of 8-Substituted Xanthines and Guanines," Tetrahedron, vol. 27, pp. 5969-5978 (1971).

Blackburn et al., "Adenosine Mediates IL-13-Induced Inflammation and Remodeling in the Lung and interacts in an IL13-Adenosine Amplification Pathway," J. Clin. Invest. vol. 112, No. 3, pp. 332-344 (2003).

Bruns, "Adenosine Antagonism by Purines, Pteridines and Benzopteridines in Human Fibroblasts," Biochemical Pharmacology, vol. 30, No. 4, pp. 325-333 (1981).

Buckle et al., "Inhibition of Cyclic Nucleotide Phosphodiesterase by Derivatives of 1,3-Bis(cyclopropylmethyl)xanthine," J. Med. Chem., vol. 37, pp. 476-485 (1994).

Cerqueira, "The Future of Pharmacologic Stress: Selective A2A Adenosine Receptor Agonists," Am. J. Cardiol., vol. 94 (2A), pp. 33D-42D (2004).

(Continued)

Primary Examiner — Lawrence E Crane
(74) Attorney, Agent, or Firm — Sheppard Mullin Richter & Hampton, LLP

(57) ABSTRACT

The present invention provides a method of myocardial perfusion imaging using reduced doses of (1-{9-[(4S,2R,3R,5R) 3,4-dihydroxy-5-(hydroxymethyl)oxolan-2-yl]-6-aminopurin-2-yl}pyrazol-4-yl)-N-methylcarboxamide.

5 Claims, 11 Drawing Sheets

(56) References Cited

U.S. PATENT DOCUMENTS

| | | | |
|---|---|---|---|
| 5,854,081 A | 12/1998 | Linden et al. | |
| 5,877,180 A | 3/1999 | Linden et al. | |
| 5,939,543 A | 8/1999 | Morozumi et al. | |
| 6,026,317 A | 2/2000 | Verani | |
| 6,117,878 A | 9/2000 | Linden | |
| 6,214,807 B1 | 4/2001 | Zablocki et al. | |
| 6,294,522 B1 | 9/2001 | Zablocki et al. | |
| 6,322,771 B1 | 11/2001 | Linden et al. | |
| 6,368,573 B1 | 4/2002 | Leung | |
| 6,387,913 B1 | 5/2002 | Mustafa | |
| 6,403,567 B1 | 6/2002 | Elzein et al. | |
| 6,448,235 B1 | 9/2002 | Linden et al. | |
| 6,514,949 B1 | 2/2003 | Linden et al. | |
| 6,552,023 B2 | 4/2003 | Zablocki et al. | |
| 6,599,283 B1 | 7/2003 | Marzilli et al. | |
| 6,605,597 B1 | 8/2003 | Zablocki et al. | |
| 6,642,210 B1 | 11/2003 | Zablocki et al. | |
| 6,670,334 B2 | 12/2003 | Linden et al. | |
| 6,677,336 B2 | 1/2004 | Zablocki et al. | |
| 6,770,634 B1 | 8/2004 | Zablocki et al. | |
| 6,825,349 B2 | 11/2004 | Kalla et al. | |
| 6,855,818 B2 | 2/2005 | Zablocki et al. | |
| 6,916,804 B2 | 7/2005 | Castelhano et al. | |
| 6,977,300 B2 | 12/2005 | Kalla et al. | |
| 6,995,148 B2 | 2/2006 | Jones et al. | |
| 7,109,180 B2 | 9/2006 | Zablocki et al. | |
| 7,109,203 B2 | 9/2006 | Hart et al. | |
| 7,125,993 B2 | 10/2006 | Elzein et al. | |
| 7,144,872 B2 | 12/2006 | Zablocki et al. | |
| 7,183,264 B2 | 2/2007 | Zablocki et al. | |
| 7,553,823 B2 | 6/2009 | Zablocki et al. | |
| 7,582,617 B2 | 9/2009 | Belardinelli et al. | |
| 7,655,636 B2 | 2/2010 | Gordi et al. | |
| 7,655,637 B2 | 2/2010 | Zablocki et al. | |
| 7,671,192 B2 | 3/2010 | Zablocki et al. | |
| 7,683,037 B2 | 3/2010 | Belardinelli | |
| 7,732,595 B2 | 6/2010 | Zablocki et al. | |
| 7,956,179 B2 | 6/2011 | Zablocki et al. | |
| 8,071,566 B2 | 12/2011 | Belardinelli et al. | |
| 8,106,029 B2 | 1/2012 | Gordi et al. | |
| 8,133,879 B2 | 3/2012 | Belardinelli et al. | |
| 8,183,226 B2 | 5/2012 | Belardinelli | |
| 8,536,150 B2 * | 9/2013 | Belardinelli et al. | 514/46 |
| 2002/0012946 A1 | 1/2002 | Belardinelli et al. | |
| 2003/0235555 A1 | 12/2003 | Shealey et al. | |
| 2004/0038928 A1 | 2/2004 | Zablocki et al. | |
| 2004/0137533 A1 | 7/2004 | Belardinelli et al. | |
| 2005/0020915 A1 | 1/2005 | Belardinelli et al. | |
| 2006/0159621 A1 | 7/2006 | Barrett | |
| 2006/0159627 A1 | 7/2006 | Zeng et al. | |
| 2007/0265445 A1 | 11/2007 | Zablocki et al. | |
| 2007/0299089 A1 | 12/2007 | Belardinelli et al. | |
| 2008/0170990 A1 | 7/2008 | Lieu et al. | |
| 2008/0213165 A1 | 9/2008 | Lieu et al. | |
| 2008/0267861 A1 | 10/2008 | Lieu et al. | |
| 2009/0081120 A1 | 3/2009 | Lieu et al. | |
| 2010/0081810 A1 | 4/2010 | Zablocki et al. | |
| 2010/0086483 A1 | 4/2010 | Belardinelli et al. | |
| 2010/0160620 A1 | 6/2010 | Zablocki et al. | |
| 2012/0251440 A1 | 10/2012 | Belardinelli et al. | |

FOREIGN PATENT DOCUMENTS

| | | |
|---|---|---|
| CA | 2377746 | 12/2000 |
| EP | 0 354 638 | 2/1990 |
| EP | 0 386 683 | 9/1990 |
| JP | SHO 48-26038 | 8/1973 |
| JP | Hei 5 1993 9197 | 1/1993 |
| WO | WO 92/00297 | 1/1992 |
| WO | WO 92/12260 | 7/1992 |
| WO | WO 93/23401 | 11/1993 |
| WO | WO 93/25677 | 12/1993 |
| WO | WO 95/11681 | 5/1995 |
| WO | WO 98/52611 | 11/1998 |
| WO | WO 98/57651 | 12/1998 |
| WO | WO 99/63938 | 12/1999 |
| WO | WO 00/78778 | 12/2000 |
| WO | WO 00/78779 | 12/2000 |
| WO | WO 01/16134 | 8/2001 |
| WO | WO 01/62979 | 8/2001 |
| WO | WO 03/088978 | 10/2003 |
| WO | WO 2004/011010 | 2/2004 |
| WO | WO 2005/082379 | 9/2005 |
| WO | WO 2006/044856 | 4/2006 |
| WO | WO 2006/076698 | 7/2006 |
| WO | WO 2007/092372 | 8/2007 |
| WO | WO 2008/028140 | 3/2008 |
| WO | WO 2008/042796 | 4/2008 |
| WO | WO 2008/063712 | 5/2008 |
| WO | WO 2008/086096 | 7/2008 |
| WO | WO 2008/143667 | 11/2008 |
| WO | WO 2009/076580 | 6/2009 |
| WO | WO 2010/037122 | 4/2010 |

OTHER PUBLICATIONS

Cline et al., "Coronary Artery Angiography Using Multislice Computed Tomography Images," Circulation, vol. 102, pp. 1589-1590, XP002564059 (2000).

Crimi et al., "Purine Derivatives in the Study of Allergic Inflammation in Respiratory Diseases," Allergy, vol. 52, No. 34, pp. 48-54 (1997).

Cristalli et al., "2-Alkynyl Derivatives of Adenosine 5'-N'ethyluronamide: Selective A2 Adenosine Receptor Agonists with Potent Inhibitory Activity on Platelet Aggretation," J. Med. Chem., vol. 37, pp. 1720-1726 (1994).

Cushley et al., "Inhaled Adenosine and Guanosine on Airway Resistance in Normal and Asthmatic Subjects," Br. J. Clin. Pharmacol, vol. 15, No. 2, pp. 161-165 (1983).

Dalpiaz et al., "De Novo Analysis of Receptor Binding Affinity Data of Xanthine Adenosine Receptor Antagonists," Arzneim-Forsch/Drug Res., vol. 45, No. 3, pp. 230-233 (1995).

Dhalla et al., "Tachycardia Caused by A2A Adenosine Receptor Agonists is Mediated by Direct Sympathoexcitation in Awake Rates," Journal of Pharmacology and Experimental Therapeutics, USA, vol. 316, No. 2, pp. 695-702, XP009073100 (2006).

Driver et al., "Adenosine in Bronchoalveolar Lavage Fluid in Asthma," Am. Rev. Respir. Dis., vol. 148, No. 1, pp. 91-97 (1993).

Elias et al., "Airway Remodeling in Asthma," The Journal of Clinical Investigation, vol. 104, No. 8, pp. 1001-1006 (1999).

Erickson et al., "1,3,8-Trisubstituted Xanthines. Effects of Substitution Pattern upon Adenosine Receptor $A_1/A_2$ Affinity", J. Med. Chem., vol. 34, pp. 1431-1435 (1991).

Feoktistov et al., "Adenosine $A_{2B}$ Receptors: A Novel Therapeutic Target in Asthma," Trends Pharmacol. Sci., vol. 19, pp. 148-153 (1998).

Feoktistov et al., "Hypoxia Modulates Adenosine Receptors in Human Endothelial and Smooth Muscle Cells Toward an A2B Angiogenic Phenotype," Hypertension, vol. 44, No. 5, pp. 649-654, Epub 2004, PMID: 15452028 [PubMed—indexed for MEDLINE] (2004).

Gao et al., "Novel Short-Acting A2A Adenosine Receptor Agonists for Coronary Vasodilation: Inverse Relationship between Affinity and Duration of Action of A2A Agonists," Journal of Pharmacology and Experimental Therapeutics, vol. 298, pp. 209-218 (2001).

Glover et al., "Characterization of a New, Highly Selective Adenosine A2A Receptor Agonist with Potential Use in Pharmacologic Stress Perfusion Imaging", Circulation, vol. 110, pp. I-311 (1999).

Glover et al., "Pharmacological Stress Thallium Scintigraphy with 2-cyclohexylmethylidenehydrazinoadenosine (WRC-0470)," Circulation, vol. 94, pp. 1726-1732 (1996).

Harvey, S.C., "Blood, Fluids, Electrolytes and Hematologic Drugs," Remington's Pharmaceutical Sciences, Chapter 40, 18$^{th}$ Ed., Gennaro et al. (eds.), Mack Publishing Co., Easton, PA, pp. 800-821 (1990).

Hendel et al. "Initial Clinical Experience with Regadenoson, a Novel Selective A2A Agonist for Pharmacologic Stress Single-Photon

(56) References Cited

OTHER PUBLICATIONS

Emission Computed Tomography Myocardial Perfusion Imaging", Journal of the American College of Cardiology, vol. 46, No. 11, pp. 2069-2075 (2005).
Hendel et al., "Pharmacologic Stress SPECT Myocardial Perfusion Imaging with a Selective A2A Agonist: Results of a Pilot Study Comparing Adenosine with CVT-3146", Circulation, Supplement IV, vol. 108, pp. 2892 (2003).
Holgate et al., "Roles of Cysteinyl Leukotrienes in Airway Inflammation, Smooth Muscle Function and Remodeling," J. Allergy Clin. Imunol. (Supp1):S18-34; discussion S34-6, Review, PMID:12532084 [PubMed—indexed for MEDLINE] (2003).
Hoshino, "Impact of Inhaled Corticosteriods and Leukotrience Receptor Antagonists on Airway Remodeling," Clinical Reviews in Allergy & Immunology, vol. 27, No. 1, pp. 59-64 (2004).
Iskandrian, "Adenosine Myocardial Perfusion Imaging," The Journal of Nuclear Medicine, vol. 35, pp. 734-736 (1994).
Jacobson et al., "1,3-Dialkylxanthine Derivatives Having High Potency as Antagonists at Human $A_{2B}$ Adenosine Receptors," Drug Development Research, vol. 47, pp. 45-53 (1999).
Jadbabaie et al., "Myocardial perfusion imaging with a novel selective A2A Adenosine Receptor Agonists (CVT-3146): Important differences in radiotracer behavior," Journal of Am. Col. Cardiology, vol. 41, pp. 443-444 (2003).
Jeffery, "Remodeling in Asthma and Chronic Obstructive Lung Disease," Am. J. Respir. Crit. Care Med., vol. 164, No. 10pt2, pp. S28-S38 (2001).
Katsushima et al., "Structure-Activity Relationships of 8-Cycloalkyl-1,3-dipropylxanthines as Antagonist of Adenosine Receptors," J. Med. Chem., vol. 33, pp. 1906-1910 (1990).
Kerensky et al. "Dose Dependent Increase in Human Coronary Blood Flow Velocity Following an IV Bolus of CVT-3146, A Novel A2A Adenosine Receptor Agonists: A Potential Agent for the Use in Pharmacological Stress Testing for Myocardial Perfusion Imaging", Circulation, Supplemental II, vol. 106, vol. 19, p. II-618, (2002).
Kim et al., "Acyl-Hydrazide Derivatives of a Xanthine Carboxylic Congener (XCC) as Selective Antagonists at Human $A_{2B}$ Adenosine Receptors", Drug Development Research, vol. 47, pp. 178-188 (1999).
Kleiner, "Reactions of Some 8-(3-Pyridyl)-6-thioxanthines with Methyl Iodide," pp. 739-743 (1973).
Klotz et al., "Comparative pharmacology of human adenosine receptors subtypes-characterization of stably transfected receptors in CHO cells," Nauny-Schmideberg's Arch Pharmacol., vol. 357, pp. 1-9 (1998).
Koepfli et al., "Interaction of caffeine with regadenoson-induced hyperemic myocardial blood flow as measured by PET", European, Heart Journal, vol. 27, No. Supp. 1, p. 175, (2006).
Korolkovas, Essentials of Molecular Pharmacology-Background for Drug Design, Wiley—Interscience, New York, NY, only pp. 266-272 supplied, (1970).
Kubo et al., "Effect of Caffeine Intake on Myocardial Hyperemic Flow Induced by Adenosine Triphosphate and Dipyridamole," The Journal of Nuclear Medicine, vol. 45, No. 5, pp. 730-738, (2004).
Leigh et al., "Is Interleukin-1 3 Critical in Maintaining Airway Hyperresponsiveness in Allergen-Challenged Mice?" Am. J. Respir. Crit. Care Med., PMID: 15242841 [PubMed—indexed for MEDLINE] vol. 170, No. 8, pp. 851-856 (2004).
Kusmic et al., "Coronary microcirculatory vasoconstriction induced by low-flow ischemia in mouse hearts is reversed by an A2A adenosine receptor", FASEB Journal, pp. A1227-A1228 (2007).
Linden et al., "Characterization of Human $A_{2B}$ Adenosine Receptors: Radioligand Binding, Western Blotting and Coupling to Gq in Human Embryonic Kidney 293 Cells and HMC-1 Mast Cells," Molecular Pharmacology, vol. 56, pp. 705-713 (1999).
Mager et al., "Molecular Simulation Applied to 2-(N'-alkylidenehydrazino)-and 2-(N'aralkylidenehydrazino) adenosine A2 Agonists," European Journal of Medicinal Chemistry, vol. 30, pp. 15-25 (1995).
Mann et al., "Airway Effects of Purine Nucleosides and Nucleotides and Release with Bronchial Provocation in Asthma," J. Appl. Physiol., vol. 61, No. 5, pp. 1667-1676 (1986).
Martin et al., "Pharmacology of 2-cylohexylmethylidenehydrazionoadenosine (WRC-0470), a novel, short-acting adenosine A-2A receptor agonist that produces selective coronary vasodilation", Drug Development Research, vol. 40, No. 4, pp. 313-324, (1997).
Marumoto et al., "Synthesis and Coronary Vasodilating Activity of 2-Substituted Adenosines," Chemical Pharmaceutical Bulletin, vol. 23, No. 4, pp. 759-774 (1975).
Marumoto et al., "Synthesis and Enzymatic Activity of Adenosine 3',5'-Cyclic Phosphate Analogues," Chemical Pharmaceutical Bulletin, vol. 27, No. 4, pp. 990-1003 (1979).
Matsuda et al., "Nucleosides and Nucleotides, 103. 2-Alkynyladenoines: A Novel Class of Selective Adenosine A2 Receptor Agonists with Potent Antihypertensive Effects," Journal of Medicinal Chemistry, vol. 35, No. 1, pp. 241-252 (1992).
Mosselhi et al., "Reactions of some 8-diazoxanthine derivatives", Indian Journal of Chemistry, vol. 33B, pp. 236-242 (1994).
Niiya et al., "2-(N'-Alkylidenehydrazino) Adenosines; Potent and Selective Coronary vasodilators," Journal of Medicinal Chemistry, American Chemical Society, vol. 35, No. 24, pp. 4557-4561, (1992).
Ogden, et al., Mean Body Weight, Height, and Body Mass Index, United States 1960-2002, U.S. National Health and Nutrition Examination Survery, Advance Data No. 347, pp. 1-18, (2004).
Persson et al., "Synthesis and Antiviral Effects of 2-Heteroaryl Substituted Adenosine and 8-Heteroaryl Guanosine Deriviatives," Bioorganic & Medicinal Chemistry, vol. 3, No. 10, pp. 1377-1382 (1995).
Pfizer, "Health info.", (2003), http://www.pfizer.be/English/What_we_do_/Health_info/COPD.htm.
Pifferi et al., "Montelukast and Airway Remodeling in Children with Chronic Persistent Asthma: An Open Study," Pediatric Allergy and Immunology, vol. 15, No. 5, pp. L472-L473 (2004).
Polosa et al., "Evolving Concepts on the Value of Adenosine Hyperresponsiveness in Asthma and Chronic Obstructive Pulmonary Disease". Thorax, vol. 57, No. 7, pp. 649-654 (2002).
Polosa, "Adenosine-Receptor Subtypes: The Relevance to Adenosine-Mediated Responses in Asthma and Chronic Obstructive Pulmonary Disease," The European Respiratory Journal: Official Journal of the European Society for Clinical Respiratory Physiology., vol. 20, No. 2, pp. 488-496 (2002).
Riou et al., "Influence of propranolol, enalaprilat, verapamil, and caffeine on adenosine A(2A) receptor medicated coronary vasodilation", Journal of the American College of Cardiology, vol. 40, No. 9, pp. 1687-1690 (2002).
Roth et al., "8-Dicyclopropylmethyl)-1,3-dipropylxanthine: A Potent and Selective Adenosine A1 Antagonist with Renal Protective and Diuretic Activities," J. Med. Chem., vol. 34, No. 1, pp. 466-469 (1991).
Ryzhov et al., "Adenosine-Activated Mast Cells Induce IgE Synthesis by B Lymphocytes: An $A_{2B}$—Mediated Process Involving the Cytokines IL-4 and IL-13 with Implications for Asthma," vol. 172, No. 12, pp. 7726-7733, PMID: 15187156 [PubMed—indexed for MEDLINE] (2004).
Sambuceti et al., "Coronary Vasoconstriction During Myocardial Ischemia Induced by Rises in Metabolic Demand in Patients with Coronary Artery Disease," *Circulation*, 1997, vol. 95, pp. 2652-2659.
Sambuceti et al., Interaction Between Coronary Artery Stenosis and Coronary Microcirculation in Ischemic Heart Disease, Z. Kardiol., 2000, vol. 89, Suppl. 9, pp. 126-131.
Shimada et al., "8-Polycycloalkyl-I,3-dipropylxanthines as Potent and Selective Antagonists for A1-Adenosine Receptors," J. Med. Chem., vol. 35, pp. 924-930 (1992).
Spicuzza et al., "The Role of Adenosine as a Novel Bronchoprovocant in Asthma," Curr. Opin. Allergy Clin. Immunol., vol. 3, No. 1, pp. 65-69 (2003).
Spicuzza et al., "Research Applications and Implications of Adenosine in Diseased Airways," Trends Pharmacol. Sci., vol. 24, No. 8, pp. 409-413, Review, PMID: 12915050 [Pubmed—indexed for MEDLINE] (2003).

(56) References Cited

OTHER PUBLICATIONS

Swinyard et al., "Pharmaceutical Necessities," Remington's Pharmaceutical Sciences, Chapter 66, 18$^{th}$ Ed., Gennaro et al. (eds.), Mack Publishing Co., Easton, PA, pp. 1318-1319 (1990).
Swinyard et al., "Pharmaceutical Necessities," Remington's Pharmaceutical Sciences, Chapter 66, 18$^{th}$ Ed., Gennaro et al. (eds.), Mack Publishing Co., Easton, PA, pp. 1286-1329 (1990).
Tomita et al., Artificial Neural Network Approach for Selection of Susceptible single Nucleotide Polymorphisms and Construction of Prediction Model on Childhood allergic Asthma: BMC Bioinformatics, vol. 1, No. 5, p. 120, PMID: 15339344 [PubMed—indexed for MEDLINE] (2004).
Trochu et al., "Selective A2A Adenosine Receptor Agonist as a Coronary Vasodilator in Conscious Dogs: Potential for Use in Myocardial Perfusion Imaging," Journal of Cardiovascular, vol. 41, No. 1, pp. 132-139 (2003).
Udelson et al., "Randomized, Controlled Dose-Ranging Study of the Selective Adenosine $A_{2A}$ Receptor Agonist Binodenoson for Pharmacological Stress as an Adjunct to Myocardial Perfusion Imaging," Circulation, vol. 209, pp. 457-464 (2004).
Van Der Wenden et al., "Mapping the Xanthine C8-region of the adenosine $A_1$ Receptor with Computer Graphics," European Journal of Pharmacology—Molecular Pharmacology Section, vol. 206, No. 1, pp. 315-323 (1991).
Xu et al., Coronary Vasodilation by a Short Acting, Low Affinity A2A Adenosine Receptor Agonist in Anesthetize Closed Chest Dogs: A Second Generation of Coronary Artery Pharmacologic Stressor, Circulation, vol. 102, No. 18, p. 3912 (2000).
Zablocki et al., "2 Substituted PI System Derivatives of Adenosine That Are Coronary Vasodilators Acting Via the A2A Adenosine Receptor," *Nucleosides, Nucleotides and Nucleic Acids*, 2001, vol. 20, Nos. 4-7, pp. 343-360.
Zhao et al., "Caffeine attenuates the duration of coronary vasodilation and changes in hemodynamics induced by regadenoson (CVT-3146), a novel adenosine A2A receptor agonist," Journal of Cardiovascular Pharmacology, Raven Press, New York, NY, vol. 49, No. 6, pp. 369-375, XP009094871 (2007).
Zhao et al., "Comparative Profile of Vasodilation by CVT-3146, a novel $A_{2A}$ receptor agonist and adenosine in conscious dogs," Journal of Pharm & Experimental Therapeutics, Journal of Pharm. & Experimental Therapeutics, vol. 41, pp. 182-189 (2003).
Zhao et al., "Effects of caffeine on coronary vasodilation and sinue tachycardia induced by Regadenoson, a novel adenosine A2A receptor agonist, in conscious dogs," European Heart Journal, vol. 27, No. Suppl. 1, p. 424 (2006).
Zhao et al., "Regadenoson, a novel pharmacologic stress agent for use in myocardial perfusion imaging, does not have a direct effect on the QT interval in conscious dogs," Journal of Cardio Vascular Pharmacology, pp. 467-473, vol. 52, No. 5, Lippincott Williams and Wilkins, USA, XP8117431 (2008).
Zhong et al., "Synergy Between A2B Adenosine Receptors and Hypoxia in Activating Human Lung Fibroblasts," American Journal of Respiratory Cell and Molecular Biology, vol. 32, No. 1, pp. 2-8 (2005).
Office Action for U.S. Appl. No. 11/766,964, dated Apr. 7, 2011, 16 pages.
Office Action for U.S. Appl. No. 11/848,743, dated Jun. 20, 2012, 14 pages.
Office Action for U.S. Appl. No. 11/864,437, dated Mar. 29, 2011, 12 pages.
Office Action for U.S. Appl. No. 11/969,047, dated Mar. 17, 2011, 13 pages.
Office Action for U.S. Appl. No. 12/163,099, dated Jun. 20, 2012, 14 pages.
Office Action for U.S. Appl. No. 12/569,643, dated Aug. 25, 2011, 9 pages.
Office Action for U.S. Appl. No. 12/569,643, dated Mar. 20, 2012, 11 pages.
Office Action for U.S. Appl. No. 12/637,583, dated Apr. 4, 2011, 10 pages.
Office Action for U.S. Appl. No. 12/695,096, dated Apr. 14, 2011, 8 pages.
Office Action for U.S. Appl. No. 12/695,096, dated Oct. 5, 2011, 6 pages.
Office Action for U.S. Appl. No. 12/749,328, dated Jun. 8, 2011, 17 pages.
Office Action for U.S. Appl. No. 12/765,623, dated Mar. 8, 2011, 7 pages.
Office Action for U.S. Appl. No. 12/968,110, dated Aug. 3, 2011, 9 pages.
Office Action for U.S. Appl. No. 13/092,812, dated Oct. 25, 2011, 6 pages.
Office Action for U.S. Appl. No. 13/333,789, dated Jul. 3, 2012, 9 pages.

\* cited by examiner

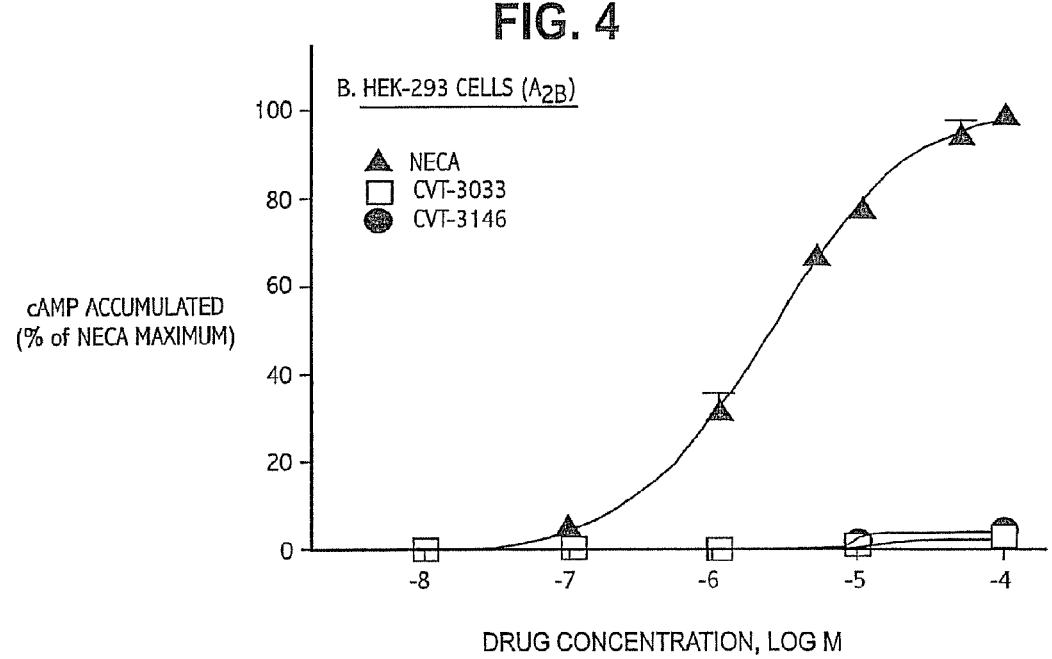
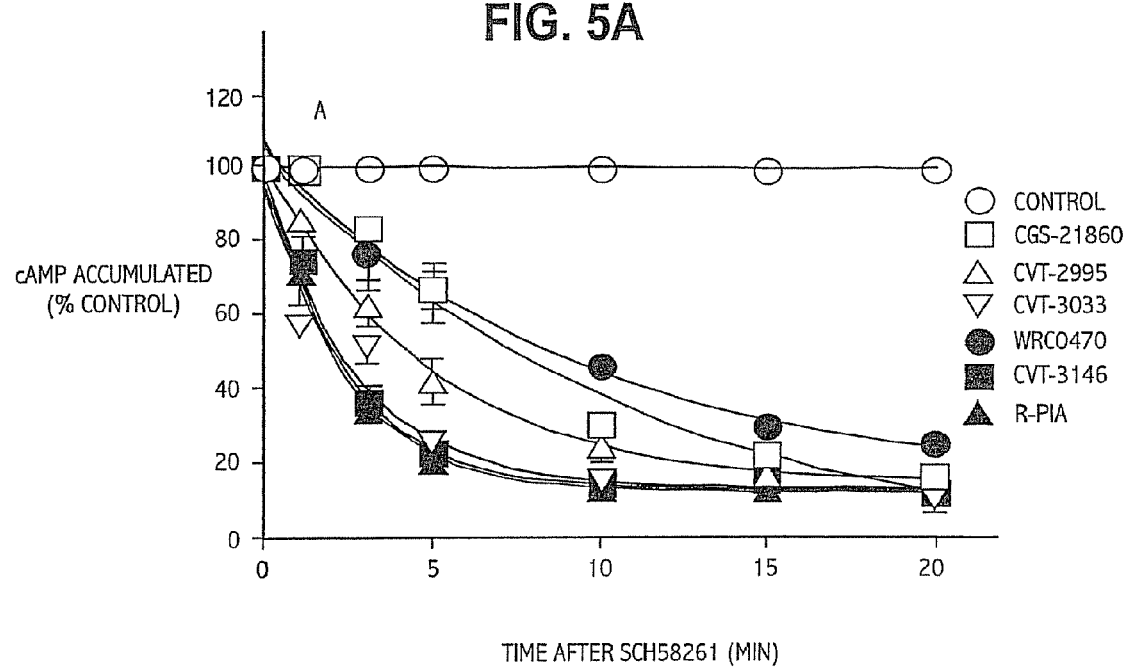

METHODS OF MYOCARDIAL PERFUSION IMAGING

This application is a continuation of U.S. patent application Ser. No. 13/525,223, filed Jun. 15, 2012, now U.S. Pat. No. 8,536,150, which is a continuation of U.S. patent application Ser. No. 13/286,069, filed Oct. 31, 2011, now abandoned, which is a continuation of U.S. patent application Ser. No. 12/435,176, filed May 4, 2009, now U.S. Pat. No. 8,071,566, which is a continuation of U.S. patent application Ser. No. 11/070,768, filed Mar. 2, 2005, now U.S. Pat. No. 7,582,617, which is a continuation of U.S. patent application Ser. No. 10/614,702, filed Jul. 3, 2003, now abandoned, which is a continuation of U.S. patent application Ser. No. 09/792,617, filed Feb. 23, 2001, now abandoned, which claims the benefit of the filing dates of Provisional Patent Application Ser. Nos. 60/219,876, filed Jul. 21, 2000 and 60/184,296, filed Feb. 23, 2000, the specifications of each of which are incorporated herein by reference.

FIELD OF THE INVENTION

This invention relates to a method of identifying compounds that are selective partial $A_{2A}$-adenosine receptor agonists, preferably with a short duration of action. Such compounds provide coronary dilation in mammals without causing corresponding significant peripheral vasodilation. The invention also relates to a method of using such compounds as adjuncts in cardiac imaging.

BACKGROUND

Myocardial perfusion imaging (MPI) is a diagnostic technique useful for the detection and characterization of coronary artery disease. Perfusion imaging uses materials such as radionuclides to identify areas of insufficient blood flow. In MPI, blood flow is measured at rest, and the result compared with the blood flow measured during exercise on a treadmill (cardiac stress testing), such exertion being necessary to stimulate blood flow. Unfortunately, many patients are unable to exercise at levels necessary to provide sufficient blood flow, due to medical conditions such as peripheral vascular disease, arthritis, and the like.

Therefore, a pharmacological agent that increases CBF for a short period of time would be of great benefit, particularly one that did not cause peripheral vasodilation. Vasodilators, for example dipyridamole, have been used for this purpose in patients prior to imaging with radionuclide. Dipyridamole is an effective vasodilator, but side effects such as pain and nausea limit the usefulness of treatment with this compound.

Adenosine, a naturally occurring nucleoside, also is useful as a vasodilator. Adenosine exerts its biological effects by interacting with a family of adenosine receptors characterized as subtypes $A_1$, $A_{2A}$, $A_{2B}$, and $A_3$. AdenoScan® (Fujisawa Healthcare Inc.) is a formulation of a naturally occurring adenosine. AdenoScan has been marketed as an adjuvant in perfusion studies using radioactive thallium-201. However, its use is limited due to side effects such as flushing, chest discomfort, the urge to breathe deeply, headache, throat, neck, and jaw pain. These adverse effects of adenosine are due to the activation of other adenosine receptor subtypes in addition to $A_{2A}$, which mediates the vasodilatory effects of adenosine. Additionally, the short half-life of adenosine necessitates multiple treatments during the procedure, further limiting its use. AdenoScan is contraindicated in many patients including those with second- or third-degree block, sinus node disease, bronchoconstrictive or bronchospastic lung disease, and in patients with known hypersensitivity to the drug.

Other potent and selective agonists for the $A_{2A}$ adenosine receptor are known. For example, MRE-0470 (Medco) is an adenosine $A_{2A}$ receptor agonist that is a potent and selective derivative of adenosine. WRC-0470 (Medco) is an adenosine $A_{2A}$ agonist used as an adjuvant in imaging. These compounds, which have a high affinity for the $A_{2A}$ receptor, and, consequently, a long duration of action, which is undesirable in imaging.

Thus, there is still a need for a method of producing rapid and maximal coronary vasodilation in mammals without causing corresponding peripheral vasodilation, which would be useful for myocardial imaging with radionuclide agents. Preferred compounds would be selective for the $A_{2A}$ adenosine receptor and have a short duration of action (although longer acting than compounds such as adenosine), thus obviating the need for multiple dosing.

Selective $A_{2A}$ receptor agonists are well known; for example, see Provisional Patent Application Ser. Nos. 60/184,296 and 60/219,876. The compounds disclosed therein have a high specificity for the adenosine $A_{2A}$ receptor subtype but are not necessarily selective to heart. We have discovered a method for identifying $A_{2A}$ receptor agonists that produce the desired vasodilation in the heart but do not significantly affect the peripheral vasculature and have a short duration of action.

In addition to discovering a method to identify $A_{2A}$ agonists that are selective coronary vasodilators, we have discovered that compounds that meet our criteria that would be superior as adjuncts to MPI techniques.

Additionally, in the above-identified Provisional Patent Application Ser. Nos. 60/184,296 and 60/219,876 the effective dose of the compounds is disclosed to be in the range of 0.01-100 mg/kg/day. Surprisingly, we have discovered that the compounds are active at much lower doses (0.0002-0.009 mg/kg) than those disclosed as effective in Accordingly, a novel and effective method of using the compounds is provided, which is virtually free of undesirable side effects.

SUMMARY OF THE INVENTION

In a first aspect, the invention relates to a method for identifying compounds useful as adjuncts in MPI, comprising the steps;

a. measuring the intrinsic efficacy of test compounds in a cell line that stably expresses adenosine $A_{2A}$ receptors.
b. measuring the intrinsic efficacy of a full agonist in said cell line.
c. selecting those compounds that have a lower intrinsic efficacy than said full agonist;
d. measuring the binding affinity ($K_i$) of the selected compounds; and
e. selecting a compound with a $K_i$>1 uM.

Such compounds are selective partial $A_{2A}$-adenosine receptor agonists, which produce coronary dilation in mammals without causing corresponding peripheral vasodilation at significant levels. They are low affinity compounds having a short duration of action.

In a second aspect, the invention relates to a method of measuring coronary blood flow (CBF) in a mammal, comprising administering to a mammal low doses of an $A_{2A}$ agonist referred to as CVT-3033, or CVT-3146.

BRIEF DESCRIPTION OF FIGURES

(FIG. 3A) PC12 cells were incubated for 10 minutes with various concentrations of adenosine receptor agonists in the presence of 50 μmol/L rolipram. Cyclic AMP levels were determined as described under "Methods". Values represent mean±SEM of results of triplicate samples from three experiments. (FIG. 3B) Effect of CVT-3033 (1 μM) on 25 CGS21680 stimulated increase cAMP accumulation in PC12 cells. PC12 cells were stimulated for 10 minutes with various concentrations of CGS21680 in the absence or presence of the partial agonist CVT-3033 (1 μM). Values represent mean±SEM of triplicate determinants from one representative experiment.

FIG. 4. Effect of CVT-3146 and CVT-3033 on cAMP content in HEK-293 cells. HEK-293 cells were incubated for 10 minutes with various concentrations of CVT-3146 or CVT-3033 in the presence of 50 μmol/L rolipram. Cyclic AMP levels were determined as described under "Methods". Values represent mean±SEM of triplicate samples from three experiments.

FIG. 5A and FIG. 5B. Time course of the decline in agonist stimulated cAMP following addition of an $A_{2A}$ adenosine receptor antagonist SCH58261. (FIG. 5A) PC12 cells were stimulated with various adenosine receptor agonists in the presence of 50 μmol/L rolipram at 37° C.

After a 10 minute incubation, SCH58261 (20 μmol/L) was added and cAMP content was determined at the times indicated. (FIG. 5B) Linear regression analysis of the relationship between the $T_{1/2}$ (min) and $pK_i$ for the agonists. Binding affinities were determined by measurement of the displacement of specific binding of [$^3$H]ZM241385 from membranes prepared from PC12 cells using the data from Table 2.

DETAILED DESCRIPTION

Definitions and General Parameters

Figure 1A:
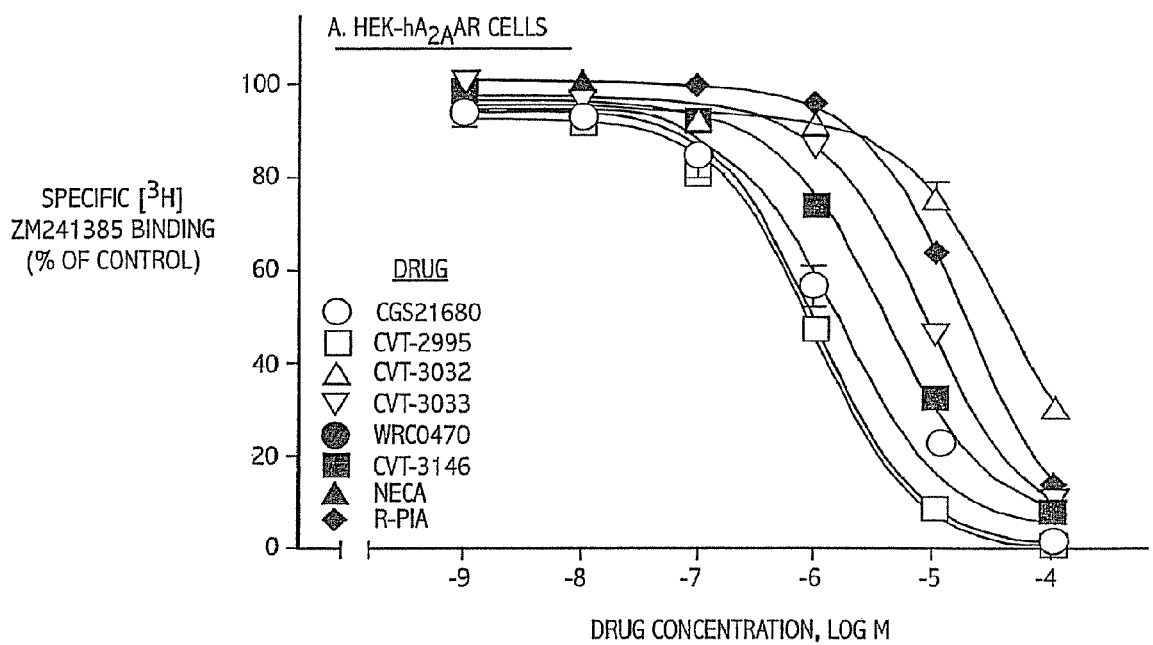
FIG. 1A and FIG. 1B. Competitive radiolabeling binding assays of adenosine receptor agonists for $A_{2A\ and}\ A_1$ binding sites. Membranes prepared from HEK-293 expressing human $A_{2A}$ adenosine receptors were incubated with [$^3$H]ZM241385 (1.5-5 M) and from $10^9$M-$10^{-5}$M of the various agonists (FIG. 1A). Membranes from CHO-K1 cells expressing human $A_1$ adenosine receptors were incubated with [$^3$H]CPX (2.5-3.0 M) and from $10^{-9}$M-$10^{-5}$M of the various agonists (FIG. 1B). The cells were incubated for two hours at room temperature in 50 mmol/L Tris-HCl buffer (pH 7.4) containing ADA (1 U/mL) and 100 μM Gpp(NH)p. Non-specific binding of [$^3$H]ZM241385 or [$^3$H]CPX was determined in the presence of either 100 μmol/L NECA or 1 μmol/L CPX, respectively. Each point represents the mean±SEM of triplicates pooled from at least three experiments. Values of $K_i$ and $pK_i$ are given in Table 2.
Figure 1B:
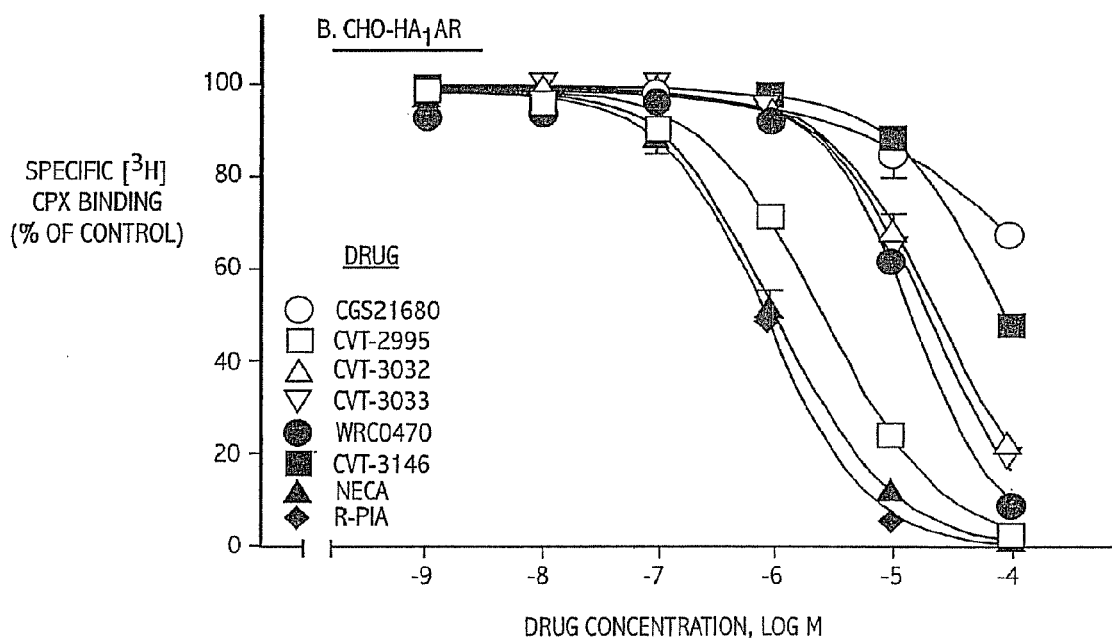

This invention provides methods for identifying partial adenosine $A_{2A}$ receptor agonists, which are particularly useful in MPI.

The interaction of an adenosine $A_{2A}$ agonist with the extracellular domain of its receptor causes a cascade of intracellular responses that culminate with vasodilation. However, there are quantitative differences in the ability of various agonists to achieve this effect With respect to drug design, the ideal agent for imaging would have a duration of action that is brief enough not to cause serious side effects, but long enough to obviate the necessity for multiple treatments. It would be selective for the $A_{2A}$ receptor, thus avoiding side effects due to interaction with other adenosine subtypes, and it would produce coronary vasodilation without causing corresponding peripheral vasodilation.

Compounds that act as $A_{2A}$ agonists produce a variety of effects that depend on both the characteristics of the agonist, its receptor, and the tissue bearing $A_{2A}$ receptors. Factors relating to agonist properties are the intrinsic efficacy (E) and the equilibrium dissociation constant of the agonist-receptor complex ($K_d$).

Intrinsic efficacy (maximal efficacy) is the maximum effect that an agonist can produce if the dose is taken to its maximum. Efficacy is determined mainly by the nature of the receptor and its associated effector system. By definition, partial agonists have a lower maximal efficacy than full agonists.

The $K_d$ of a drug is obtained from data generated from a saturation experiment analyzed according to a Scatchard plot (B/F versus F), which leads to a linear curve. The $K_d$ is estimated as the negative reciprocal of the slope of the line of best fit, and $B_{max}$ by the abscissa intercept of the line. The reciprocal of $K_d$ measures the affinity constant ($K_a$) of the radioligand for the receptor. Thus, for a given ligand-receptor pair, the smaller the $K_d$ (0.1-10 nM) the higher its affinity. $B_{max}$ is expressed as pmol or fmol per mg tissue or protein.

When the saturation experiment is performed in the presence of a displacer (competitor), the line of best fit of the Scatchard plot can be modified in a manner that depends on the type of receptor interaction exhibited by the displacer. Two main cases exist: (1) decreased slope and unchanged $B_{max}$, the displacement is of the competitive type; (2) unchanged slope and unchanged displacement of the non-competitive type. Intermediate cases where both the slope and $B_{max}$ are modified also exist.

Data generated from a displacement experiment are generally fitted by a sigmoidal curve termed the displacement or inhibition curve, that is the percentage radiolabeled ligand specifically bound versus log [displacer] in M). The abscissa of the inflexion point of the curve gives the $IC_{50}$ value, the concentration of displacer that displaces or inhibits 50% of the radioactive ligand specifically bound. $IC_{50}$ is a measure of the inhibitor or affinity constant (Ki) of the displacer for the receptor. $IC_{50}$ and $K_i$ are linked as follows if the displacement is of the competitive type then $$K_i = IC_{50}/(1+[C^*]/K_d^*)$$

This is the Cheng-Prusoff equation (Biochem. Pharmacol, 22:3099 (1973)). [C*] is the concentration of radioligand and $K_d^*$ is its dissociation constant. The duration of the biological effect of an agonist is directly related to the binding affinity of a compound. It is desirable that compounds that act as adjuncts in imaging have an effect that is long enough to produce a response without repeated administration but short enough to avoid adverse side effects. Consequently, the preferred compounds of the invention will have a relatively low binding affinity and a relatively short duration of action.

The potency is the dose or concentration required to bring about some fraction of a compound's maximal effect (i.e., the amount of compound needed to produce a given effect). In graded dose-response measurements, the effect usually chosen is 50% of the maximum effect and the dose causing the effect is called the $EC_{50}$. Dose-response ratios using $EC_{50}$ values for an agonist for a given receptor in the absence and presence of various concentrations of an antagonist for the same receptor are determined and used to construct a Schild plot from which the $K_b$ and $_pA_2$ ($-\log_{10} K_b$) values are determined.

The concentration of antagonist that causes 50% inhibition is known as the $IC_{50}$. $IC_{50}$ is used to determine the $K_b$, the equilibrium dissociation constant for the antagonist-receptor complex. Thus, $$K_b = [IC_{50}]/1 + [A]/K_A$$

wherein $K_A$=equilibrium dissociation constant for an agonist binding to a receptor (concentration of agonist that causes occupancy of 50% of the receptors) and [A] is the concentration of agonist.

A compound may be potent but have less intrinsic activity than another compound. Relatively potent therapeutic compounds are preferable to weak ones in that lower concentrations produce the desired effect while circumventing the effect of concentration dependent side effects. The tissue specific factors that determine the effect of an agonist are the number of viable specific receptors in a particular tissue [RT] and the efficiency of the mechanisms that convert a stimulus (S) into an effector response. Thus, there exists for a given tissue, a complex function f (S) that determines the magnitude of the response:

$$\text{Response} = f(S) = \frac{f([A] E[RT])}{([A] + K_d)}$$

Therefore, a response to a drug is a function of both the stimulus produced by agonist interaction with the receptor and the efficiency of the transduction of that stimulus by the tissue. Stimulus is proportional to the intrinsic efficacy of the agonist and the number of receptors. Consequently, variation in receptor density in different tissues can affect the stimulus for response. Furthermore, some tissues have very efficiently coupled receptors and other relatively inefficient coupled receptors. This has been termed 'receptor reserve' (or spare receptor) since in the first case, a maximum effect can be achieved when a relatively small fraction of the receptor is apparently occupied and further receptor occupancy can produce no additional effect. The magnitude of the response will thus depend on the intrinsic efficacy value so that, by classical definition, full agonists (E=1) produce the maximum response for a given tissue, partial agonists produce a maximum response that is below that induced by the full agonist (0<E<1), and antagonists produce no visible response and block the effect of agonists (E=0). These activities can be completely dependent upon the tissue, i.e., upon the efficiency coupling. Therefore, low-efficacy adenosine agonists may be partial agonists in a given tissue and yet full agonists in peripheral arteries with respect to a function such as vasodilation.

The presence of spare receptors in a tissue increases sensitivity to an agonist. An important biologic consequence of spare receptors is that they allow agonists with low efficacy for receptors to produce full responses at low concentrations and therefore elicit a selective tissue response. Thus, a drug may be designed to elicit a maximal effect in a desired tissue but elicit a less than maximal effect in other tissues when such action of a drug would lead to undesirable side effects.

Thus, the invention provides a method of identifying drugs by first determining their efficacy compared to a known full agonist. Then, the binding affinity of the compound is determined. Compounds identified by this method will demonstrate partial agonist effects in the cAMP assays and a low $K_i$ as determined by affinity binding assays.

One preferred compound of the invention that is a selective partial $A_{2A}$-adenosine receptor agonist with a short duration of action is a compound of the formula:

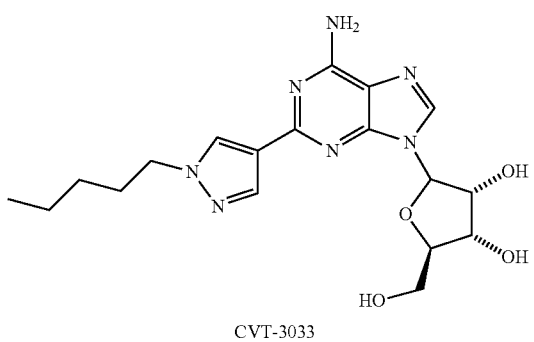 [SMILES: CCCCCn1cc(-c2nc(N)c3ncn(C4O[C@H](CO)[C@@H](O)[C@H]4O)c3n2)cn1]

CVT-3033

CVT-3033 is particularly useful as an adjuvant in cardiological imaging. The preparation of CVT-3033 and related compounds is described in U.S. patent application Ser. No. 09/338,327, filed on Jun. 22, 1999, now U.S. Pat. No. 6,214,807, the specification of which is incorporated herein by reference.

Another preferred compound of the invention that is a selective partial $A_{2A}$-adenosine receptor agonist with a short duration of action is a compound of the formula:

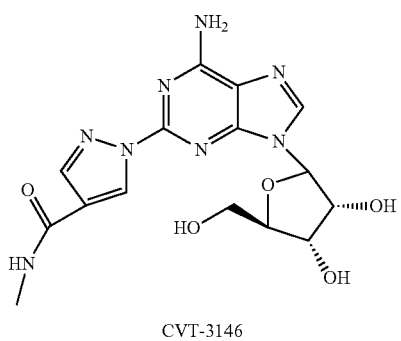 [SMILES: CNC(=O)c1cnn(-c2nc(N)c3ncn(C4O[C@H](CO)[C@@H](O)[C@H]4O)c3n2)c1]

CVT-3146

The preparation of CVT-3146 and related compounds is set forth in U.S. patent application Ser. No. 09/338,185 filed on Jun. 22, 1999, now U.S. Pat. No. 6,403,567, the specification of which is incorporated herein by reference.

Compounds identified by the method of the invention are partial $A_{2A}$ agonists that increase CBF but do not significantly increase peripheral blood flow. That is, the stimulation of blood flow in the periphery is less than 50% of the increase of that in the heart.

Preferred compounds identified by the method of the invention have a duration of less than 5 seconds but longer than the effect produced by adenosine.

The compounds identified by the method of the invention are useful $A_{2A}$ agonists that may be used as adjuncts in cardiac imaging when added either prior to dosing with an imaging agent or simultaneously with an imaging agent.

Suitable imaging agents are $^{201}$Thallium or $^{99m}$Technetium-Sestamibi, $^{99mTc}$teboroxime, and $^{99mic}$(III).

The term "optional" or "optionally" means that the subsequently described event or circumstance may or may not occur, and that the description includes instances in which said event or circumstance occurs and instances in which it does not.

The compositions may be administered orally, intravenously, through the epidermis or by any other means known in the art for administering therapeutic agents.

The method of treatment of comprises the administration of an effective quantity of the chosen compound, preferably dispersed in a pharmaceutical carrier. Dosage units of the active ingredient are generally selected from the range of 0.3 to 103 μg/kg, but will be readily determined by one skilled in the art depending upon the route of administration, age and condition of the patient. These dosage units may be administered one to ten times daily for acute or chronic disorders. No unacceptable toxicological effects are expected when compounds of the invention are administered in accordance with the present invention.

Pharmaceutical compositions including the compounds of this invention, and/or derivatives thereof, may be formulated as solutions or lyophilized powders for parenteral administration. Powders may be reconstituted by addition of a suitable diluent or other pharmaceutically acceptable carrier prior to use. If used in liquid form the compositions of this invention are preferably incorporated into a buffered, isotonic, aqueous solution. Examples of suitable diluents are normal isotonic saline solution, standard 5% dextrose in water and buffered sodium or ammonium acetate solution. Such liquid formulations are suitable for parenteral administration, but may also be used for oral administration. It may be desirable to add excipients such as polyvinylpyrrolidinone, gelatin, hydroxy cellulose, acacia, polyethylene glycol, mannitol, sodium chloride, sodium citrate or any other excipient known to one of skill in the art to pharmaceutical compositions including compounds of this invention. Alternatively, the pharmaceutical compounds may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, teffa alba, magnesium stearate or stearic acid, talc, pectin, acacia, agar or gelatin. The carrier may also include a sustained release material such as glycerol monostearate or glycerol distearate, alone or with a wax. The amount of solid carrier varies but, preferably, will be between about 20 mg to about 1 gram per dosage unit. The pharmaceutical dosages are made using conventional techniques such as milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

The Examples that follow serve to illustrate this invention. The Examples are intended to in no way limit the scope of this invention, but are provided to show how to make and use the compounds of this invention.

EXAMPLES

The following abbreviations are used in the Examples:

TABLE 1

List of Abbreviations and Activities of Experimental Compounds

| Chemical Compound | Abbreviation | Receptor/Activity |
|---|---|---|
| 4-aminobenzyl-5'-N-methylcarbox-amidoadenosine | ABMECA | $A_3$ agonist |
| adenosine deaminase | ADA | |
| 2-p-(2-carboxy-ethyl) phenethyl-amino-5'-N-ethylcarboxamido-adenosine | CGS21680: | High affinity $A_{2A}$ agonist |
| 8-cyclopentyl-1,3-dipropylxanthine | CPX | $A_1$ antagonist |
| 5'-guanylyl-imididodiphosphate | Gpp(NH)p | Stabilizes GPCR |
| 2-hexynyladenosine-5'-N-ethyl- | HENECA | |
| N-ethylcarboxamido-adenosine | NECA | Non-selective adenosine receptor agonist |
| Phenylisopropyladenosine | R-PIA | $A_1$ receptor agonist |
| Rolipram | | phosphodiesterase inhibitor |
| | SCH58261: | $A_{2A}$ antagonist |
| 2-cyclohexylmethylidenehydrazinoadenosine | WRC-0470: | High affinity 2A agonist |
| 4-(2-[7-amino-2-(2 furyl) [1,2,4]-triazolo[2,33-a][1,3,5]triazin-5-yl amino]ethyl)phenol | ZM241385: | 2A antagonist |

Other abbreviations include cAMP (cyclic adenosine monophosphate), APV (average peak velocity), CBF (coronary blood flow), CHO-Ki (Chinese hamster ovary cell line), HEK-293 (human cell line), CPP (coronary perfusion pressure), CR (coronary resistance), HR (heart rate), im (intramuscular), iv (intravenous) LVSP (left ventricle systolic pressure), MAP (mean arterial pressure). PBF (peripheral blood flow).

Adenosine deaminase was purchased from Boehringer Mannheim Biochemicals Indianapolis, Ind.). [$^3$H] ZM241385 was purchased from Tocris Cookson Ltd (Langford, Bristol, UK). [$^3$H]CPX was from New England Nuclear (Boston, Mass.). HENECA CGS21680, adenosine, NECA, R-PIA, phenylephrine, DMSO, rolipram and HEK-hA$_{2A}$AR membranes were obtained from Sigma-RBI (Natick, Mass.). Nitroglycerin was obtained from Parke-Davis, Morris Plains, N.J. Aminophylline was obtained from Abbott Laboratories, Chicago, Ill.

HENECA was a gift from Professor Gloria Cristalli of the University of Camerino, Italy. Drug stock solutions (10 mmol/L) were prepared in DMSO. Sprague Dawley rats were purchased from Simonsen Laboratories (Gilroy, Calif.). Ketamine was purchased from Fort Dodge Animal Health (Fort Dodge, Iowa) and xylazine from Bayer (Shawnee Mission, Kans.). Succinyl cAMP-tyrosyl methyl ester (ScAMP-TME) was purchased from Sigma and iodinated in the presence of chloramine T. CVT-2995, CVT-3003—((4S,2R,3R,5R)-2-(6-amino-2-(2-thienyl)purin-9-yl)-5-(hydroxymethyl)ox-olane-3,4-diol), CVT-3006—((4S,2R,3R,5R)-2-(6-amino-2-{3-[2-benzylphenoxy]prop-1-ynyl}purin-9-yl)-5-(hydroxymethyl)oxolane-3,4-diol), CVT-3032, CVT-3033, CVT-3100—((4S,2R,3R,5R)-2-[6-amino-2-(5-methyl(2-thienyl))purin-9-yl]-5-(hydroxymethyl)oxolane-3,4-diol), CVT-3101—(4-(3-{9-[(4S,2R,3R,5R)-3,4-dihydroxy-5-(hydroxymethyl)oxolan-2-yl]-6-aminopurin-2-yl}prop-2-ynyloxy)benzenecarbonitrile), CVT-3126—(4S,2R,3R,5R)-2-{6-amino-2-[1-(3-phenylpropyl)pyrazol-4-yl]purin-9-yl}-5-(hydroxymethyl)oxolane-3,4-diol), CVT-3127—(ethyl 1-{9-[(4S,2R,3R,5R)-3,4-dihydroxy-5-(hydromethyl)ox-olan-2-yl]-6-aminopurin-2-yl}pyrazole-4-carboxylate), CVT-3141—((4S,2R,3R,5R)-2-{6-amino-2-[4-(4-chlorophenyl)pyrazole]purin-9-yl}-5-(hydroxymethyl)oxolane-3,4-diol), CVT-3144—((4S,2R,3R,5R)-2-{6-amino-2-[4-(4-methylphenyl)pyrazolyl]purin-9-yl}-5-(hydroxymethyl)oxolane-3,4-diol), CVT-3146, YT-146 and WRC0470 were synthesized by CV Therapeutics, Department of Medicinal and Bioorganic Chemistry, Palo Alto, Calif. The structures of several of these compounds are set forth on the following page.

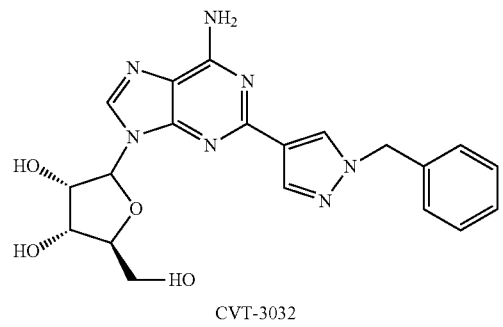

CVT-3032

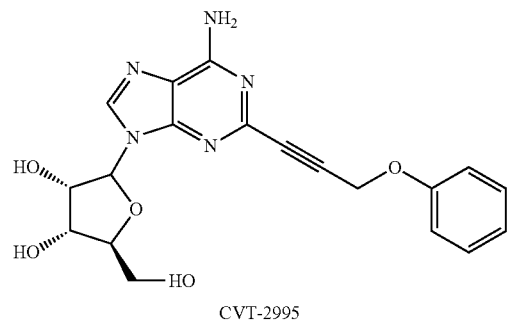

CVT-2995

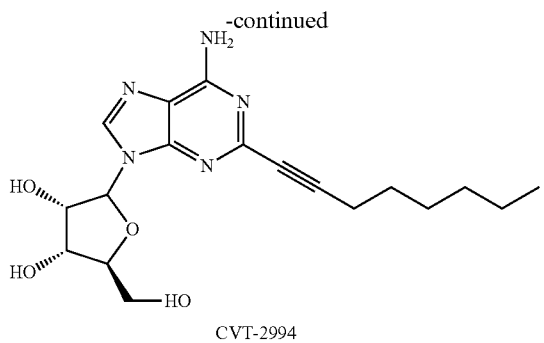

CVT-2994

Examples 1 and 2

Examples 1 and 2 demonstrate the selectivity and binding affinity of the compounds of the invention to adenosine receptors on cells obtained as follows. Rat pheochromocytoma PC12 cells were obtained from the American Type Culture Collection and grown in DMEM with 5% fetal bovine serum, 10% horse serum, 0.5 mmol/L L-glutamine, 100 U/mL penicillin, 0.1 mg/mL streptomycin, and 2.5 μg/mL amphotericin.

HEK-293 cells stably expressing recombinant human $A_{2A}$ adenosine receptors (HEK-h$A_{2B}$ adenosine receptors) were grown in DMEM supplemented with 10% fetal bovine serum and 0.5 mg/mL, G-418.

CHO-K1 cells stably expressing the recombinant human $A_1$ adenosine receptors (CHO-h$A_1$ adenosine receptors) or $A_3$ adenosine receptors (CHO-h$A_3$ adenosine receptors) were grown as monolayers on 150-mm plastic culture dishes in Ham's F-12 media supplemented with 10% fetal bovine serum in the presence of 0.5 mg/mL G-418. Cells were cultured in an atmosphere of 5% $CO_2$/95% air and maintained at 37° C.

Cell membranes were harvested from the cell lines by detaching cells from the culture plates into ice-cold 50 mmol/L Tris-HCl buffer (pH 7.4). The cell suspensions were homogenized and centrifuged at 48,000 g for 15 minutes. The pellets were washed three times by re-suspension in ice-cold Tris-HCl buffer and centrifugation. The final pellet was resuspended in Tris-HCl, aliquoted and frozen at −80° C. until used for receptor binding assays.

The protein concentration of membrane suspensions was determined using the Bradford (Bradford, M. M. (1976. Anal. Biochem. 72, 248) with bovine serum albumin as standard.

Membranes were also obtained from porcine striatial cells as follows. Porcine striatum was obtained from Pel Freeze Inc. Striatum was minced and homogenized in 10 volumes of ice-cold 50 mmol/L Tris HCl buffer (pH 7.4). The homogenate was filtered through cotton gauze and centrifuged at 48,000 g for 15 minutes at 4° C. The supernatant was discarded, and the membrane pellet was suspended in 10 volumes of 50 mmol/L Tris-HC 1 buffer (pH 7.4) and washed three times by centrifugation and resuspended in fresh buffer. The final pellet was frozen at −80° C. until used for receptor binding assays.

Competitive radiolabeling binding assays were performed to determine the binding affinities of the compounds of the invention for the adenosine receptor subtypes, $A_1$, $A_{2A}$, $A_{2B}$, and $A_3$. Briefly, membrane suspensions, obtained from cells expressing either adenosine receptor subtypes $A_1$, $A_{2A}$, $A_{2B}$ or $A_3$ were incubated for 2 hours at room temperature in 50 mmol/L Tris-HCl buffer (pH 7.4) containing ADA (1 U/mL). [$^3$H]-ZM241385 (~1.5 to 5 nmol/L) was added to membranes from cells expressing $A_{2A}$, [$^3$H]-CPX (~2.5 to 3.0 nmol/L) was added to membranes from cells expressing $A_1$, [$^3$H]-CPX (30 nM) was added to membranes from cells expressing $A_{2B}$ and [$^{125}$I]ABMECA (1 nM)} was added to membranes from cells expressing A3. The competing agents, that is the agonists ($10^{-9}$-$10^{-4}$M) were also added along Gpp (NH) p (100 μg) which stabilizes the receptor in the low affinity state thereby obviating the complication of multiple affinity states (Gao., Z. et al. (1999). Biochem J 338(3):729). At the end of the incubation, free radioligand was separated from membrane-bound radioligand by filtration through Whatman GF/C glass fiber filters using a Brandel tissue harvester (Gaithersburg, Md.). Triplicate determinations were performed for each concentration of unlabelled compound.

The results of radioligand binding assays, presented in Table 2, show that binding affinities of CVT-3033 (1417 nM) and CVT-3146 (1095 nM) to $A_{2A}$ receptors in pig striatum were lower (i.e. $K_i$ higher) than a full $A_{2A}$ agonist, CGS21680 (157 nM).

Figure 2A:
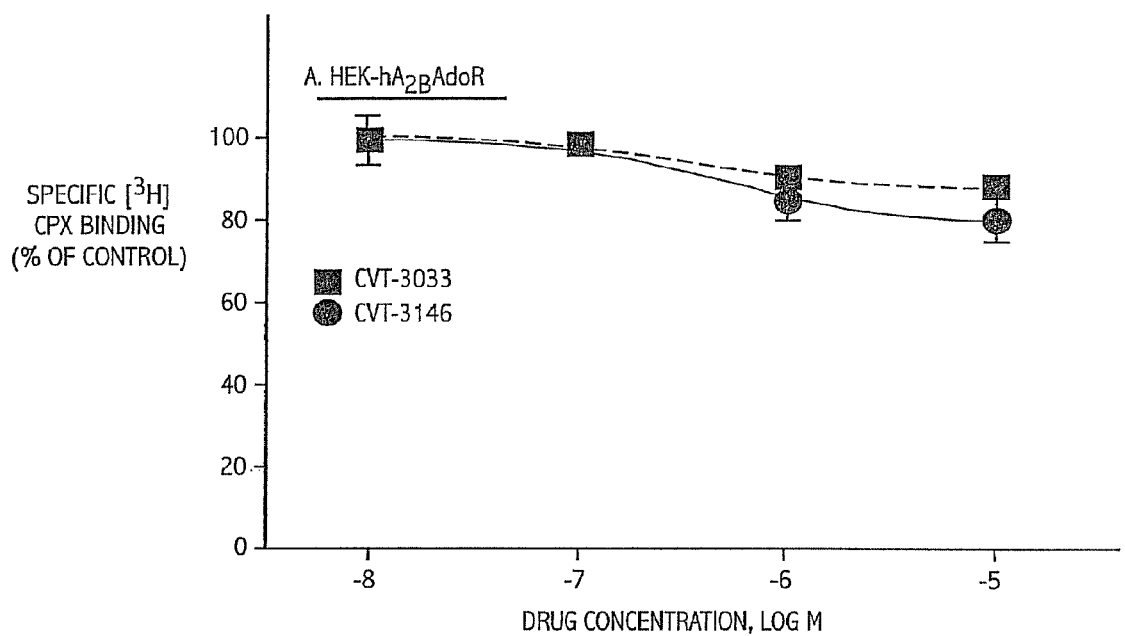
FIG. 2A and FIG. 2B. Competitive radiolabeling binding assays of adenosine receptor agonists for $A_{2b\ and}\ A_3$ binding site. Membranes suspensions from HEK-293 cells expressing $A_{2b}$ adenosine receptors were incubated with [$^3$H]DPCPX (1.5-5 M) and from $10^{-8}$M-$10^{-5}$ M of the various agonists (FIG. 2A). Membranes from CHO-K1 cells expressing $A_3$ adenosine receptors were incubated with [$^{125}$I]ABMECA (2.5-3.0 M) and from $10^{-8}$M-$10^{-5}$M of the various agonists (FIG. 2B). The cells were incubated for two hours at room temperature in 50 mmol/L Tris-HCl buffer (pH 7.4) containing ADA (1 U/mL). Each point represents the mean±SEM of triplicates pooled from three experiments.
Figure 2B:
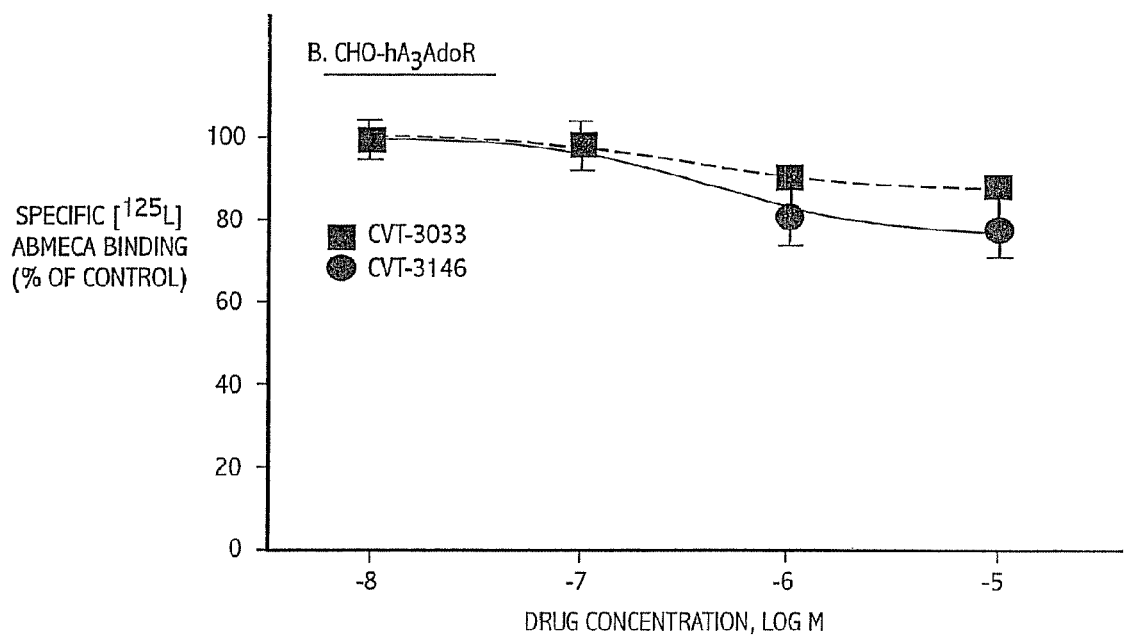

The binding affinities of CVT-3033 (3623 nM) and CVT-3146 (1734 nM) to $A_{2A}$ were also lower than CGS21680 (210 nM) in PC12 cells. Binding affinities of CVT-3033 (2895 nM) and CVT-3146 (1269 nM) were also lower than CGS21680 (609 nM) in HEK cells expressing human $A_{2A}$ receptors. CGS-21680, CVT-3033, and CVT-3146 had relatively low affinities for the $A_1$ receptor expressed by CHO-K1 cells. Binding to the $A_{2A}$ receptor was relatively greater than binding affinities to $A_1$, $A_2$b or $A_3$ (FIGS. 1A and B and FIGS. 2A and B).

TABLE 2

Binding affinity of adenosine receptor agonists for $A_{2A}$ and $A_1$ AdoRs

| | $K_i$, nmol/L (p$K_i$ ± SEM) | | | |
|---|---|---|---|---|
| Compounds | Pig Striatum ($A_{2A}$) Affinity N | PC12 cells ($A_{2A}$) Affinity N | HEK-h$A_{2A}$AdoR Affinity N | CHO-h$A_1$AdoR Affinity N |
| NECA | ND | 297 (6.54 ± 0.06) 4 | 360 (6.45 ± 0.06) 3 | 328 (6.49 ± 0.06) 3 |
| R-PIA | 1106 (5.96 ± 0.06) 4 | 3476 (5.48 ± 0.10) 3 | 1656 (5.78 ± 0.02) 3 | 477 (6.45 ± 0.11) 3 |
| CGS21680 | 157 (6.85 ± 0.23) 5 | 210 (6.74 ± 0.09) 3 | 609 (6.22 ± 0.06) 3 | 3540 (5.47 ± 0.20) 3 |
| CVT-2995 | 14.4 (7.86 ± 0.12) 4 | 53 (7.28 ± 0.05) 4 | 305 (6.52 ± 0.04) 6 | 866 (6.07 ± 0.05) 3 |
| WRC0470 | 20.7 (7.68 ± 0.04) 3 | 18 (7.77 ± 0.04) 8 | 272 (6.55 ± 0.04) 6 | 7278 (5.16 ± 0.09) 3 |
| CVT-3032 | 1594 (5.88 ± 0.10) 3 | 5516 (5.26 ± 0.05) 3 | 13651 (4.87 ± 0.02) 3 | 6350 (5.22 ± 0.11) 3 |

TABLE 2-continued

Binding affinity of adenosine receptor agonists for $A_{2A}$ and $A_1$ AdoRs

| | $K_i$, nmol/L (p$K_i$ ± SEM) | | | |
|---|---|---|---|---|
| Compounds | Pig Striatum ($A_{2A}$) Affinity N | PC12 cells ($A_{2A}$) Affinity N | HEK-h$A_{2A}$AdoR Affinity N | CHO-h$A_1$AdoR Affinity N |
| CVT-3033 | 1417 (5.67 ± 0.16) 3 | 3623 (5.45 ± 0.03) 5 | 2895 (5.54 ± 0.03) 3 | 5836 (5.24 ± 0.04) 3 |
| CVT-3146 | 1095 (5.95 ± 0.11) 5 | 1734 (5.76 ± 0.01) 3 | 1269 (5.9 ± 0.03) 7 | >16460 (4.59 ± 0.35) 3 |
| YT-146 | 16.3 (7.86 ± 0.33) 4 | ND | ND | ND |
| CVT-3003 | 1007 (6.00 ± 0.07) 3 | ND | ND | ND |
| CVT-3006 | 64 (7.24 ± 0.26) 3 | ND | ND | ND |
| CVT-3100 | 697 (6.16 ± 0.06) 5 | ND | ND | ND |
| CVT-3101 | 94 (7.03 ± 0.06) 3 | ND | ND | ND |
| CVT-3126 | 1667 (5.78 ± 0.09) 3 | ND | ND | ND |
| CVT-3127 | 64 (7.22 ± 0.17) 3 | ND | ND | ND |
| CVT-3141 | 1138 (5.95 ± 0.07) 3 | ND | ND | ND |
| CVT-3144 | 502 (6.31 ± 0.12) 3 | ND | ND | ND |
| HENECA | 7.96 (8.10 ± 0.08) 10 | ND | ND | ND |

The binding affinities of adenosine receptor agonists for $A_{2A}$AdoRs and $A_1$AdoRs were determined by their effect to compete with specific binding of [$^3$H]ZM241385 or [$^3$H]CPX, respectively, to membranes from the indicated tissue/cells.
Values are means ± SEM of results of at least three experiments (n) performed in triplicate.
Numbers in parentheses are means of p$K_i$ ± SEM.
Values of the equilibrium dissociation constant ($K_d$) for [$^3$H]ZM241385 binding that were used in calculations of $K_i$ values were 0.5, 0.5 and 0.8 nM for pig striatum, PC12 and HEK-h$A_{2A}$AdoR cells, respectively.
A $K_d$ value of 1 nM for [$^3$H]CPX binding to CHO-h$A_1$AdoR membrane was used in calculation of $K_i$ values is 1.

Example 3

Example 3 demonstrates the ability of the compounds of the invention to stimulate cAMP levels, a measure of the intrinsic efficacy of the agonists. Briefly, PC12 cells were rinsed three times with Hanks' balanced saline solution (HBSS), detached using a cell lifter, and pelleted by centrifugation at 500 g for 5 minutes. Aliquots of the cell suspension (0.1 to 0.2 mg protein) were placed in microfuge tubes with 250 μL of HBSS containing rolipram (50 μmol/L) to inhibit phosphodiesterases that degrade cAMP and warmed to 37° C.

Appropriate drugs were added to the cell suspensions, and incubations were allowed to continue for 10 minutes. Tubes were placed in a boiling water bath for 5 minutes to terminate the incubation. The samples were then cooled to room temperature, diluted by the addition of 1 mL of 10 mmol/L Tris-HCl buffer at pH 7.4, and then centrifuged for 2 minutes at 13000 g.

The cAMP content of the supernatant was determined by modification of a radioimmunoassay method described by Harper and Brooker (1975. J. Cyclic nucleotide Res 1:207). Briefly, an aliquot of the supernatant (0.01 mL) was mixed with 0.04 mL of HBSS, 0.05 mL of 50 mmol/L sodium acetate buffer (pH 6.2) containing 10 mmol/L $CaCl_2$, [$^{125}$I] ScAMP-TME (12500 dpm), and 0.05 mL of anti-cAMP antibody (1:2000 dilution with 0.1% bovine serum albumin in distilled water). The samples were then incubated at 4° C. for 16 hours. At the end of the incubation, 70 μL of a 50% (wt/vol) hydroxyapatite suspension was added to each tube. The suspensions were gently agitated and then incubated for 10 minutes at 4° C. Antibody-bound radioactivity adsorbed to hydroxyapatite was collected onto glass fiber filters by vacuum filtration using a Brandel cell harvester. Radioactivity retained by the filter was counted in a gamma counter. Nonspecific binding of [$^{125}$I]ScAMP-TME was defined as radioactivity bound in the presence of 3 μmol/L unlabeled cAMP and was subtracted from total binding. The amount of cAMP present in samples was calculated based on a standard curve using known amounts of cAMP.

Figure 3A:
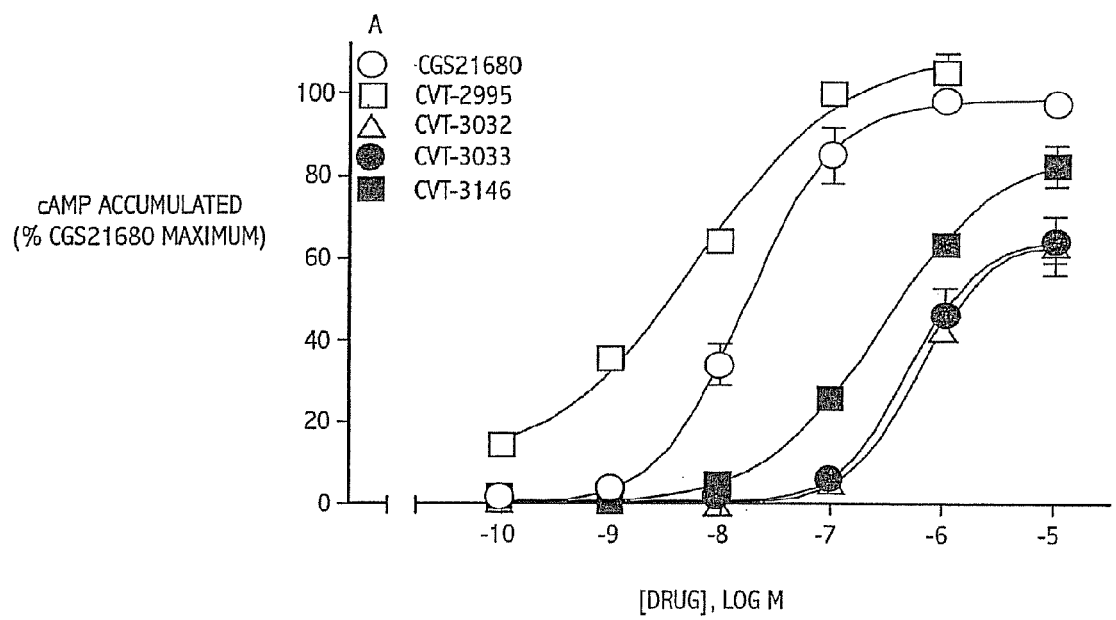
FIG. 3A and FIG. 3B. Effects of adenosine receptor agonists on cAMP content in intact PC12 cells.
Figure 3B:
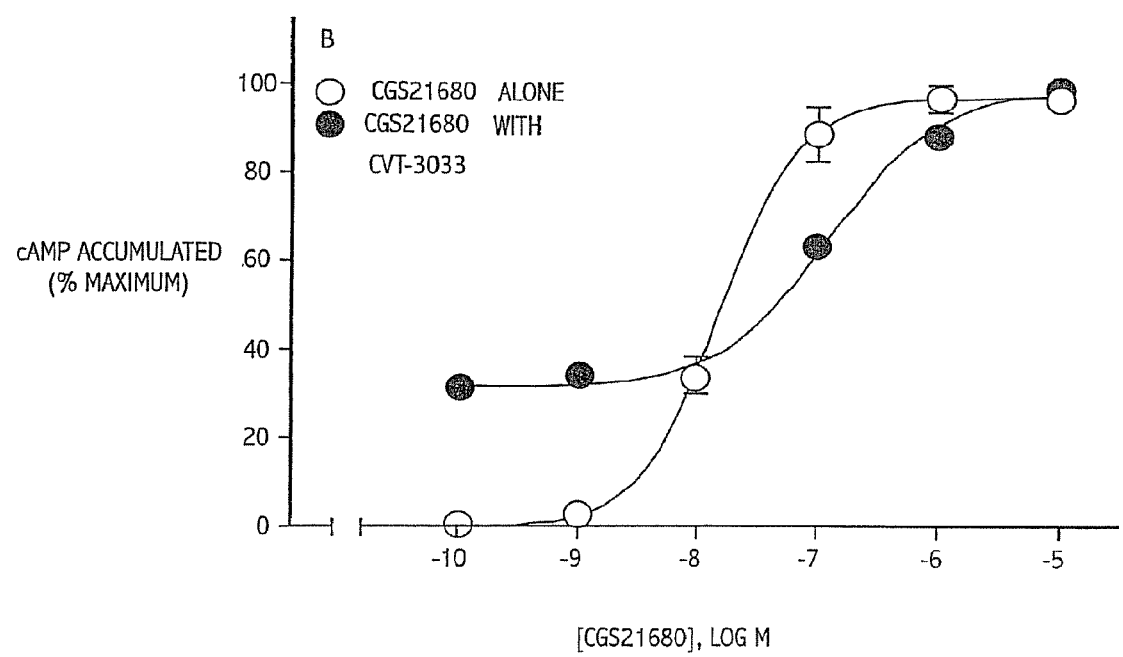

As illustrated in FIG. 3A, all compounds increased the cellular content of cAMP in a concentration-dependent manner. The low affinity $A_{2A}$ agonists CVT-3032, CVT-3033 and CVT-3146, were not only less potent (10-15 fold), but also less effective in stimulating cAMP accumulation compared to CGS21680. The maximal responses induced by CVT-3146, CVT-3033 and CVT-3032 were 85%, 63% and 65% of that induced by CGS21680, respectively. These data demonstrate that CVT-3146, CVT-3033 and CVT-3032 behave as partial $A_{2A}$ agonists in PC12 cells. Additionally, CVT-3033 (1 μM) inhibits the ability of CGS21680 to stimulate cAMP levels (FIG. 3B) causing an approximate 5-fold shift to the right of the CGS21680 concentration-response curve.

It is notable that the stimulation of cAMP levels in PC12 cells was related to the binding affinity of the compounds to $A_{2A}$ receptors (Table 3).

TABLE 3

Rate of decline ($t_{0.5}$) of cAMP accumulated after exposure to the $A_{2A}$ agonists in PC12 cells

| Agonists | $t_{0.5}$ (min) | n |
|---|---|---|
| WRC0470 | 5.9 ± 0.8 | 6 |
| CGS21680 | 5.3 ± 0.5 | 5 |
| CVT-2995 | 3.9 ± 0.6 | 5 |
| CVT-3146 | 2.6 ± 0.2 | 6 |

TABLE 3-continued

Rate of decline ($t_{0.5}$) of cAMP accumulated after
exposure to the $A_{2A}$ agonists in PC12 cells

| Agonists | $t_{0.5}$ (min) | n |
|---|---|---|
| CVT-3033 | 1.9 ± 0.1 | 4 |
| R-PIA | 1.6 ± 0.2 | 6 |

Values are mean ± SEM of the least three experiments performed in triplicate.
The $pK_i$ (−$logK_i$) values were obtained from the results of competition binding assays under [$^3$H]ZM241385 as the radioligand for $A_{2A}$ AdoRs.
The pEC50 (−logEC50) values were determined from concentration response relationships for agonist-induced cAMP accumulation in PC12 cells.
The $t_{0.5}$ values were calculated from the rate of decline of cAMP accumulated during exposure to each agonist (1 μM) following the addition of the $A_{2A}$ AdoR antagonists SCH58261 (20 μM)>.

The selectivity of the effects of CVT-3033 and CVT-3146 on cAMP accumulation in HEK-293 cells expressing $A_{2B}$ adenosine receptors is also shown. NECA, a non-selective adenosine receptors agonist, caused a concentration-dependent increase of cellular cAMP content whereas neither CVT-3033 nor CVT-3146 had any detectable effects even at a high concentration of 100 μM (FIG. 4). These results indicate that CVT-3033 and CVT-3146 have very weak, if any, interaction with $A_{2B}$ receptors.

The effect of an $A_{2A}$ antagonist on agonist-mediated cAMP accumulation in PC12 was also demonstrated. PC12 cells cultured in DMEM at 37° C. were treated with WRC0470, CGS21680, CVT-2995, CVT-3146, CVT-3033 and R-PIA each at a concentration of 1 μM in the presence of rolipram (50 μM) for 10 minutes. Then, an $A_{2A}$ antagonist, SCH58261 (20 μM), was added and cAMP content was determined at various periods. The time for cAMP levels to decrease to half maximal ($t_{0.5}$) was calculated and plotted against the affinity ($pK_i$) of each agonist for the $A_{2A}$ adenosine receptor, as determined by competition radioligand binding assays (above).

Figure 5B:
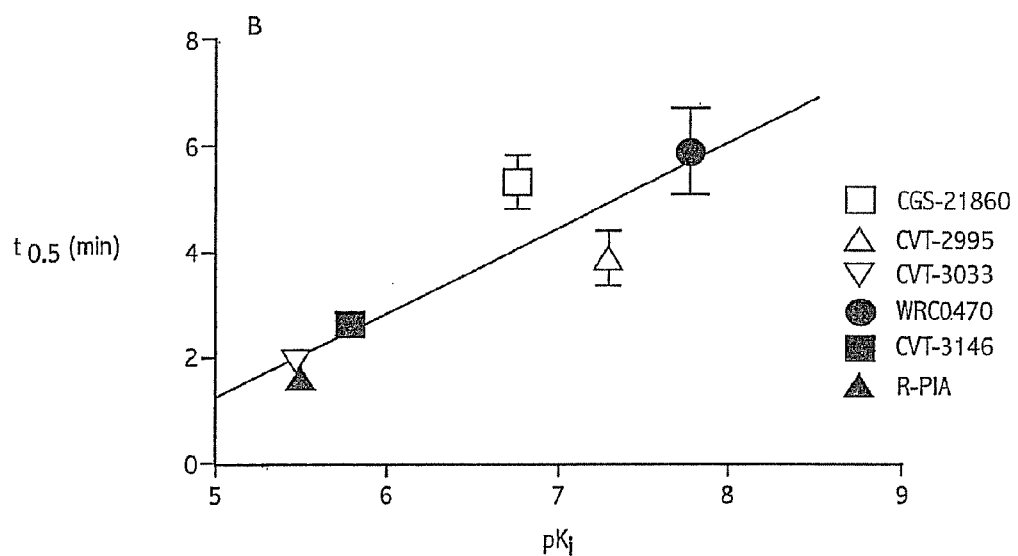

FIG. 5A shows the time-course of the decline of agonist-stimulated cAMP accumulation following the addition of SCH58261 when compared to the control cultures (CGS2160 incubated without SCH58261). The calculated values of $t_{0.5}$ from these experiments are presented in Table 3. The apparent $t_{0.5}$ values of agonists were inversely related to their affinities for $A_{2A}$ adenosine receptors, that is, the greater the agonist affinity, the lower the rate of decline of cAMP content upon application of the $A_{2A}$ adenosine receptors antagonist SCH58261 (FIG. 5A). As depicted in FIG. 5B, the relationship between the apparent $t_{0.5}$ and $pK_i$ for the agonists was best fit by linear regression with a correlation coefficient (r value) of 0.84.

Example 4

The effect of the compounds of the invention on coronary conductance (CC), an estimate of vasodilation, was demonstrated ex vivo using perfused rat hearts. Briefly, rats of either sex weighing 230-260 grams were anesthetized by intraperitoneal injection of a mixture of ketamine (100 mg/ml) and xylazine (20 mg/ml). The chest of each rat was opened and the heart removed, and rinsed in ice-cold modified Krebs-Henseleit (K-H) solution containing NaCl 117.9, KCl 4.5, $CaCl_2$ 2.5, $MgSO_4$ 1.18, $KH_2PO_4$ 1.18, pyruvate 2.0 mmol/L. The aorta was cannulated and the heart was perfused at a flow rate of 10 ml/min with modified K-H solution. The K-H solution (pH 7.4) was gassed continuously with 95% $O_2$ and 5% $CO_2$ and warmed to 35±0.5° C. The heart was electrically paced at a fixed cycle length of 240 ms (250 beats/min) using a bipolar electrode placed in the left atrium. The electrical stimuli were generated by a Grass stimulator (Model S48, W. Warwick, R.I.) and delivered through a Stimuli Isolation Unit (Model SIU5, Astro-Med, Inc., NY) as square-wave pulses of 3-msec in duration and with an amplitude of at least twice the threshold intensity.

Figure 6:
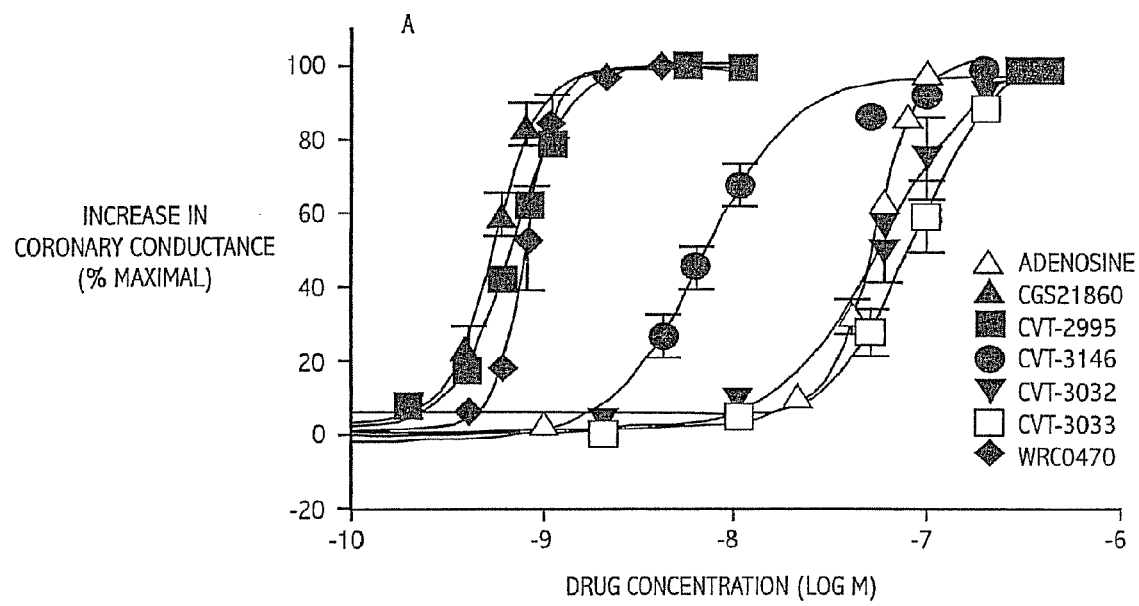
FIG. 6. Effects of adenosine receptor agonists on coronary conductance in isolated rat hearts. Concentration-dependent stimulation by CGS21680, CVT-2995, WRC0470, CVT-3146, CVT-3033, CVT-3032 and CVT-3100 of coronary conductance of isolated rat hearts. Symbols and error bars represent the mean±SEM of single determination from 4 to 6 hearts per agonist. Hearts were paced at a cycle length of 250 msec. Coronary conductance in the absence of drug was 0.17±0.01 ml/min/mmHg (mean±SEM, n=26).

As shown in FIG. 6, adenosine, CGS21680, WRC0470, and the CVT compounds caused concentration-dependent increases in coronary conductance.

The potencies ($EC_{50}$ values) of adenosine, CGS21680, WRC0470 and the CVT compounds are summarized in Table 4. The low affinity agonist CVT-3146 was found to be approximately 10-fold more potent than adenosine but 10-fold less potent than the high affinity agonists CGS21680 and WRC0470 with respect to increasing coronary conductance. The results show that CVT 3146 was a potent agonist of coronary conductance in heart but only a weak agonist in PC 12 cells ($EC_{50}$=291 nM).

TABLE 4

Potency of adenosine and $A_{2A}$ Adenosine receptor agonists
to increase cAMP accumulation in PC12 cells and coronary
conductance in rat isolated perfused heart
$EC_{50}$ ($pEC_{50}$ ± SEM), nM

| Agonist | cAMP Accumulation (PC12 cells) | | Coronary Conductance (Rat Isolated Heart) | |
|---|---|---|---|---|
| CGS21680 | 18 (7.75 ± 0.03) | N = 3 | 0.54 (9.27 ± 0.03) | N = 3 |
| CVT-2995 | 6.6 (8.82 ± 0.25) | N = 3 | 0.68 (9.17 ± 0.03) | N = 5 |
| CVT-3146 | 291 (6.54 ± 0.03) | N = 3 | 6.40 (8.19 ± 0.04) | N = 4 |
| CVT-3032 | 613 (6.21 ± 0.02) | N = 3 | 66.50 (7.18 ± 0.07) | N = 4 |
| CVT-3033 | 487 (6.31 ± 0.01) | N = 3 | 67.95 (7.19 ± 0.08) | N = 4 |
| WRC0470 | ND | | 0.62 (9.19 ± 0.6) | N = 5 |
| Adenosine | ND | | 59.20 (7.24 ± 0.11) | N = 4 |

Values are the mean concentrations of agonists that caused 50% increase in cAMP accumulation or coronary conductance ($EC_{50}$ and $pEC_{50}$).
ND; Not determined.

Figure 7A:
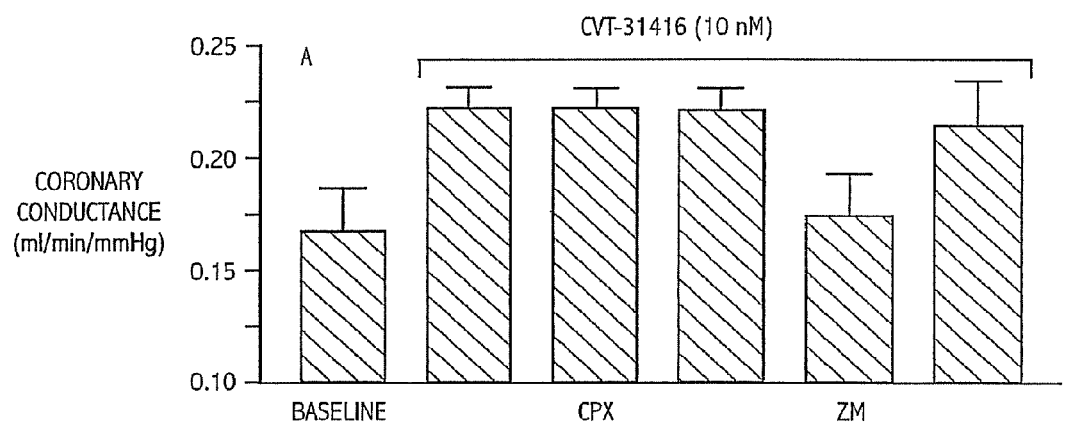
FIG. 7A. Effect of CPX and ZM241385 on CVT-3146 (10 nM) on CPP by isolated rat hearts.
Figure 7B:
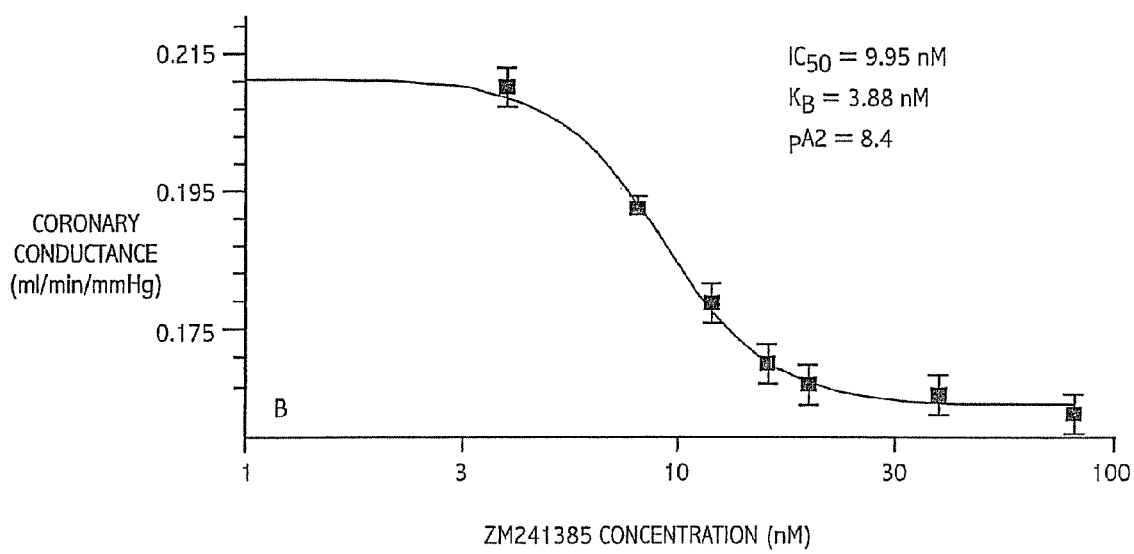
FIG. 7B. Effect of concentration of ZM241385 on CVT-3146 stimulation of CC by isolated rat hearts.

Coronary vasodilatory effect of CVT-3146 in the absence and presence of adenosine receptor antagonists were also demonstrated. The identity of the adenosine receptor subtype ($A_1$ or $A_{2A}$) mediating the coronary vasodilation was determined. Hearts (n=6) were exposed to CVT-3146 (10 nM), and after the effect of this agonist reached steady-state, CPX (60 nM), an A1 antagonist and then ZM241385 (60 nM), an A2a antagonist were added to the perfusate and the changes in CPP were recorded. As depicted in FIG. 7A, CVT-3146 significantly increased coronary conductance to 0.22±0.01 ml mm $Hg^{-1}min^{-1}$ from a baseline value of 0.16±0.02 ml mm $Hg^{-1}min^{-1}$. This increase in coronary conductance caused by CVT-3146 was not affected by 60 nM CPX but was completely reversed by 60 nM ZM241385. Furthermore, the inhibition by ZM241385 of an increase of coronary conductance caused by CVT-3146 was concentration-dependent (FIG. 7B).

$A_1$ adenosine receptor-mediated depression of A-V nodal conduction time by CVT-3033 and CVT-3146 (negative dromotropic effect) was measured using atrial and ventricular surface electrograms as described by Jenkins and Belardinelli (Circ Res 63:97).

Figure 8:
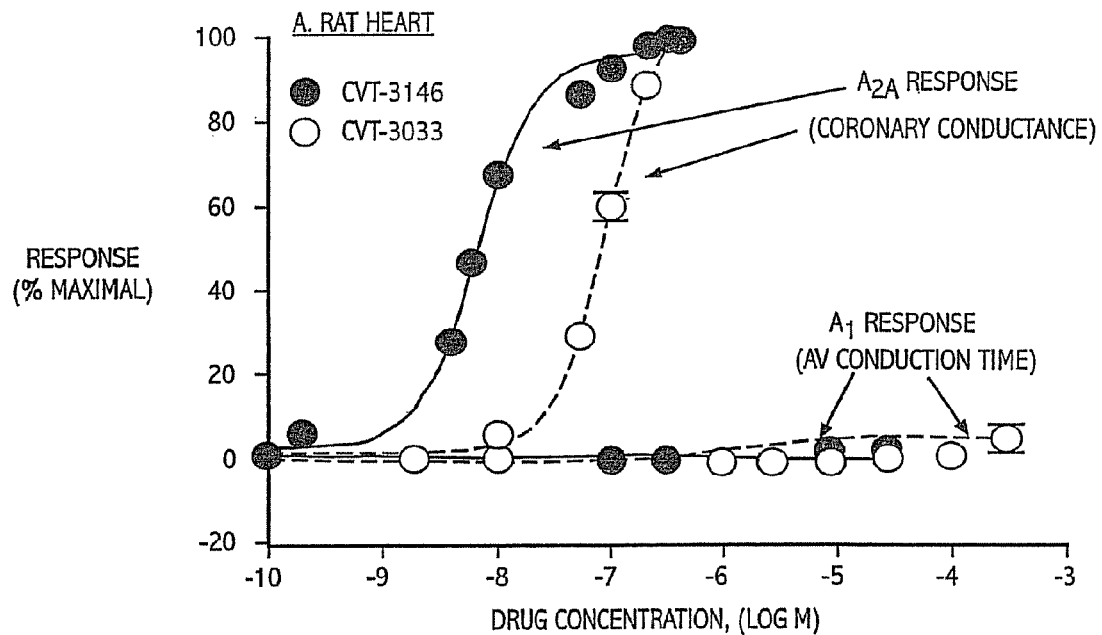
FIG. 8. Functional selectivity of CVT-3146 and CVT-3033 for adenosine receptor subtypes and the effect of concentration on AV conduction time and coronary conductance in isolated rat hearts. Symbols and error bars represent mean±SEM of single determinations from each of three hearts.

As shown in FIG. 8, CVT-3146 and CVT-3033 increased coronary conductance in a concentration-dependent manner, but did not prolong A-V nodal conduction time. Coronary perfusion pressure (CPP) was measured using a pressure transducer that was connected to the aortic cannula via a T-connector positioned approximately 3 cm above the heart. CPP was monitored throughout an experiment and recorded either on a chart recorder (Gould Recorder 2200S, Valley View, Ohio) or a computerized recording system (PowerLab/ 4S, ADInstruments Pty Ltd, Australia). Only hearts with CPP ranging from 60 to 85 mmHg (in the absence of drugs) were used in the study. CC conductance (in ml/min/mmHg) was calculated as the ratio between coronary perfusion rate (10 ml/min) and CPP.

Figure 9A:
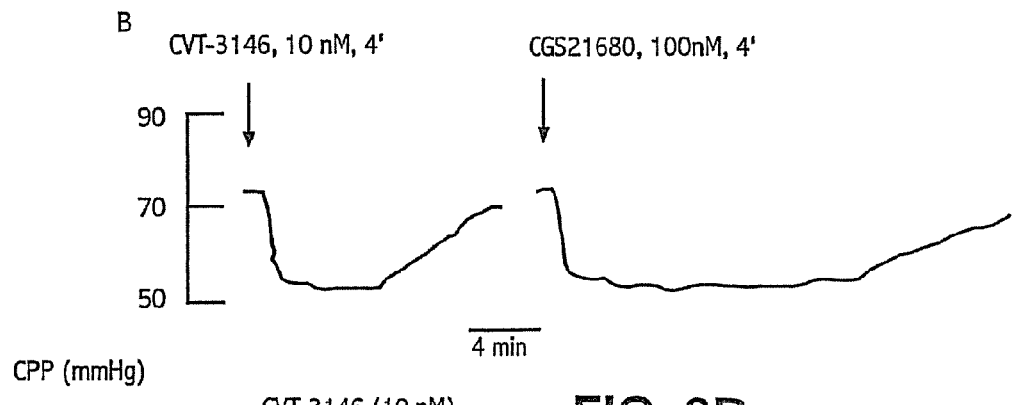
FIG. 9A and FIG. 9B. Effect of adenosine receptor agonists on coronary perfusion pressure (CPP) in isolated rat hearts. Decreases in CPP caused by infusion of CVT-3146 (10 nM, 4 min) or CGS21680 (100 nM, 4 min) (FIG. 9A and FIG. 9B). Decrease in CPP caused by the infusion of CVT-3146 (10 nM) with or without additional infusion of CGS21680 (100 nM).
Figure 9B:
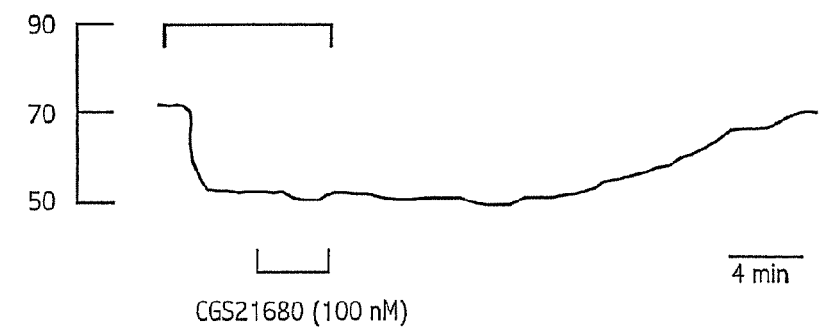

As shown in FIG. 9A the extent of the decrease in coronary perfusion pressure (an index of the coronary vasodilation) caused by CVT-3146 was similar to that caused by a supramaximal concentration of CGS21680 (FIG. 9B). Both 10 nM CVT-3146 and 100 nM CGS21680 decreased coronary perfusion pressure by 23 mmHg. In addition, in the presence of 10 nM CVT-3146, CGS21680 (100 nM) did not cause a further decrease of the coronary perfusion pressure (FIG. 9B). Thus, CVT-3146 is a full agonist with respect to coronary artery conductance.

Figure 10A:
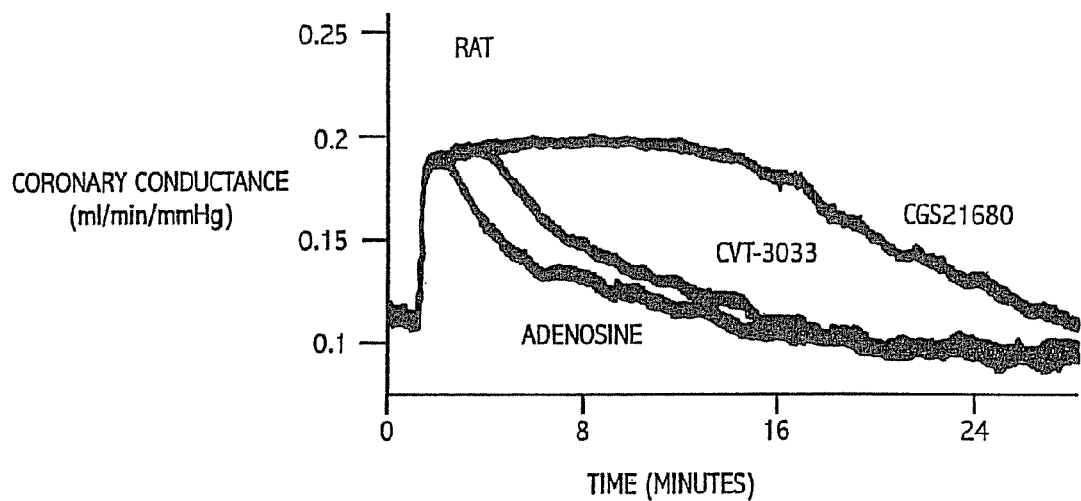
FIG. 10A and FIG. 10B. Reversal of effect of agonist stimulation on CC. CVT-3033, CGS21680 and adenosine were given as boluses by iv infusion to isolated rat hearts and then CC was measured at 8, 16 and 24 minutes after administration (FIG. 10A). Also, CVT-3146, WRC 0470 and adenosine were given as boluses by iv infusion to isolated rat hearts and then CC was measured at 8, 16 and 24 minutes after administration (FIG. 10B). Linear regression analysis of the relationship between the $pK_i$ (data from Table 2) and the reversal time ($t_{0.9}$) of coronary vasodilation are given in FIGS. 10C and D. Each data point represents the mean±SEM of $pK_i$ and $t_{0.9}$ values. R and N are the correlation coefficient and number of agonists, respectively.
Figure 10B:
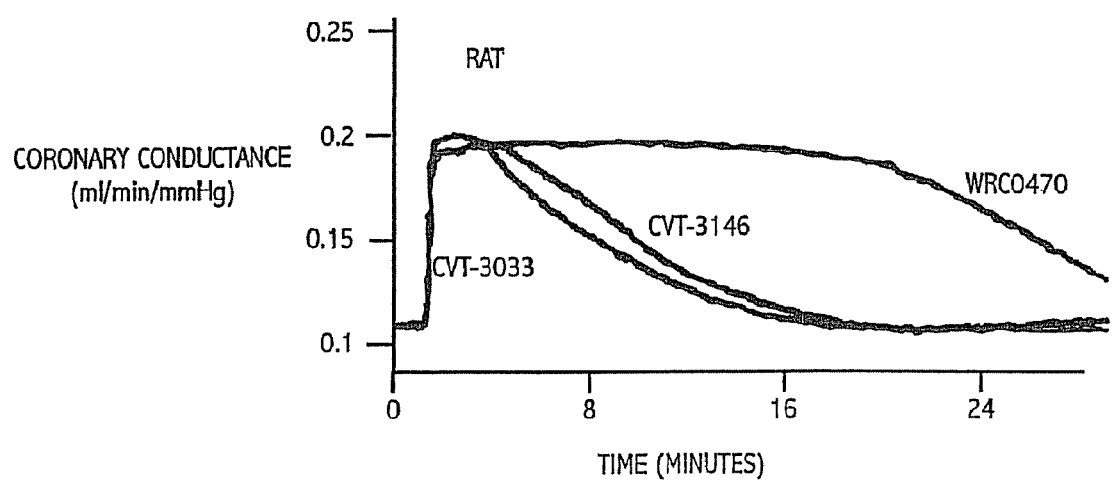
Figure 10C:
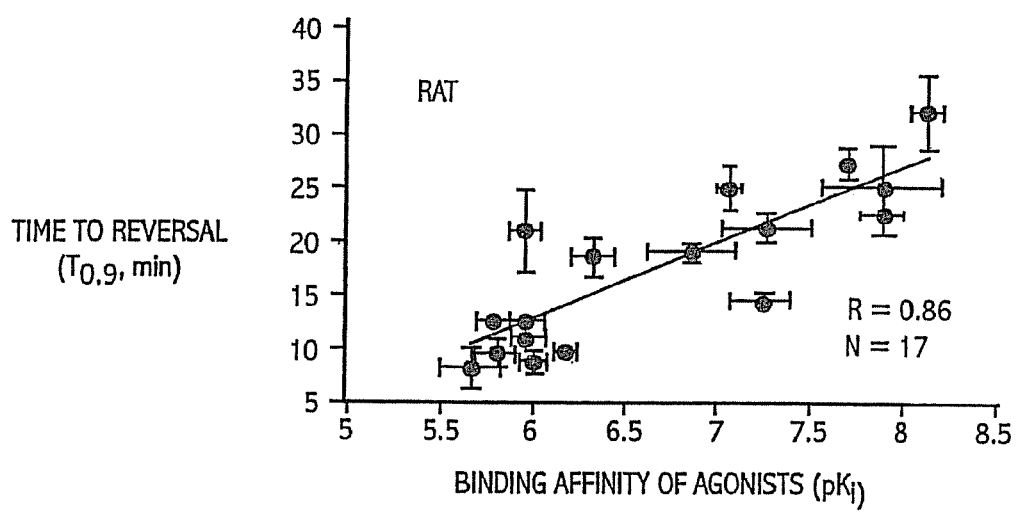

The relationship between the affinity of agonists for the $A_{2A}$ receptor and the rate of reversal of agonist-mediated responses (coronary vasodilation in heart and cAMP accumulation in PC 12 cells) upon termination of drug administration were determined. All compounds were given as boluses into the perfusion line at their respective minimal concentrations that caused equally or near-equally maximal increases in coronary conductance. Likewise, the onset and time to peak effect (i.e. maximal coronary vasodilation) were similar for all agonists. Although adenosine and the various agonists caused equal maximal increases in coronary conductance, the durations of their effects were markedly different. The duration of the effect of adenosine was the shortest followed by those of CVT-3033 and CVT-3146. The effects of CGS21680 and WRC0470 had the longest duration (FIG. 10A and FIG. 10B). The duration of the coronary vasodilation in isolated rat hearts caused by adenosine, the CVT compounds, and other agonists measured as the time to 50% and 90% ($t_{0.5}$ and $t_{0.9}$, respectively) reversal of the increases in coronary conductance after termination of drug administration are summarized in Table 4. The reversal time of coronary vasodilation correlated with the affinity of the adenosine derivatives for the $A_{2A}$ receptors. As shown in FIG. 10C, there was a significant ($p<0.05$) inverse relationship ($r=0.87$) between the affinity ($pK_i$) of the agonists for the $A_{2A}$ adenosine receptors (Table 2) and the reversal time ($t_{0.9}$) (Table 4) of the coronary vasodilation caused by the same agonists in rat isolated hearts.

Example 5

The magnitude of the effect of $A_{2A}$ adenosine receptor agonists on coronary dilation and the duration of the effect was detonated in pigs weighing 22-27 kg. All animals received humane care according to the guidelines set forth in "The Principles of Laboratory Animal Care" formulated by the National Society for Medical research and the "Guide for the Care and Use of Laboratory Animals" prepared by the Institute of Laboratory Animal Resources and published by the National Institutes of Health (NIH Publication No. 86-23, revised 1996). In addition, animals were used in accordance with the guidelines of the University of Kentucky Institutional Animal Care and Use Protocol.

Animals were anesthetized with ketamine (20 mg/kg, i.m.) and sodium pentobarbital (15-18 mg/kg, i.v.). Anesthesia was maintained with additional sodium pentobarbital (1.5-2 mg/kg, i.v.) every 15-20 minutes. Animals were ventilated via a tracheotomy tube using a mixture of room air and 100% $O_2$. Tidal volume, respiratory rate and fraction of $O_2$ in inspired air were adjusted to maintain arterial blood gas (ABG) and pH values. Core body temperature was monitored with an esophageal temperature probe and maintained at 37.0-37.5° C. by use of a heating pad. Lactate Ringers solution was administered via an ear or femoral vein as an initial bolus of 300-400 ml followed by a continuous infusion at a rate of 5-7 ml/kg/hr. A catheter was inserted into the femoral artery to monitor arterial blood pressure.

The heart was exposed through a median sternotomy and suspended in a pericardial cradle. Left ventricular pressure (LVP) was measured with a 5F high fidelity pressure sensitive tip transducer (Millar Instruments, Houston, Tex.) placed in the left ventricular cavity via an apical incision and secured with a purse string suture. A segment of the left anterior descending coronary artery (LAD), proximal to the origin of the first diagonal branch, was dissected free of surrounding tissue. A transit time perivascular flow probe (Transonic Systems Inc., Ithaca, N.Y.) was placed around this segment to measure CBF. Proximal to the flow probe, a 24-gauge modified angiocatheter was inserted for intracoronary infusions. All hemodynamic data were continuously displayed on a computer monitor and fed through a 32-bit analog to digital converter into an online data acquisition computer with customized software (Augury, Coyote Bay Instruments, Manchester, N.H.). $A_{2A}$ adenosine receptors agonists were dissolved in DMSO to produce stock concentrations of 1-5 mM, which were diluted in 0.9% saline and infused at rates of 1-1.5 ml/min via the catheter. The $A_{2A}$ adenosine receptors agonists were administered intracoronary.

Relationship between affinity of various agonists for $A_{2A}$ adenosine receptor and the reversal time of their effect to increase coronary conductance was determined in pigs. Each experiment was preceded by a 30-minute stabilization period following the completion of all instrumentation of the animal. Baseline hemodynamic data were then recorded and an intracoronary infusion of an $A_{2A}$ Adenosine receptors agonist was initiated. Each infusion was maintained for 4-5 minutes to allow LAD CBF to reach a steady-state, after which the infusion was terminated. The times to recovery of CBF by 50% ($t_{0.5}$) and 90% ($t_{0.9}$) of the difference from peak effect to baseline CBF were recorded. Ten to 15 minutes after CBF returned to pre-drug values a second infusion with a different agonist was started. In preliminary studies it was found that the intracoronary infusion of adenosine receptor agonists produced varying degrees of systemic hypotension, and hence, in all subsequent experiments, phenylephrine was administered intravenously at dose of ~1 μg/kg/min. Hemodynamic measurements were made prior to and following the initiation of the phenylephrine infusion.

The phenylephrine infusion rate was adjusted during and following the infusions of the adenosine receptor agonists to maintain arterial blood pressure within 5 mmHg of pre-infusion values. The effect of a maximum of three different agonists was determined in each experiment.

All CVT-compounds as well as CGS21680 and other $A_{2A}$ adenosine receptors agonists (i.e., WRC-0470 and YT-146) caused significant increases in CBF (Table 6).

Figure 10D:
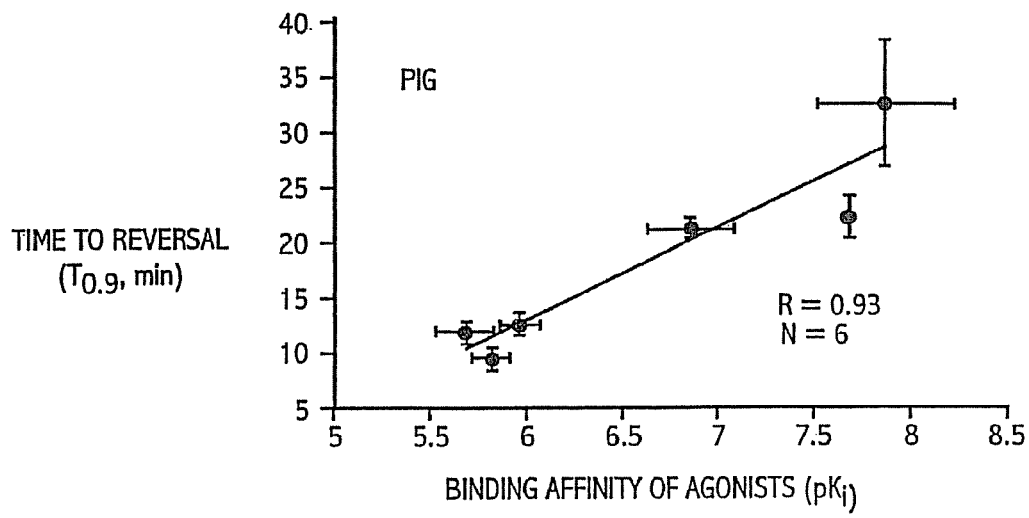

Selected doses of these compounds given as continuous (4 to 5 min) intracoronary infusions caused 3.1 to 3.8-fold increases in CBF. Once it was established that all agonists caused comparable increases of CBF (i.e., "fold increase") and caused little or no changes in heart rate and mean arterial blood pressure (data not shown), the reversal time of their coronary vasodilatory effects was determined. As summarized in Table 5 the reversal times of the effect of the low affinity, partial agonists, CVT-3146, CVT-3032 and CVT-3033, were shorter than those of CGS21680, WRC-0470 or YT-146. More importantly, as depicted in FIG. 10D, there was a significant ($p<0.05$) inverse relationship ($r=0.93$) between the affinity ($pK_i$) of the $A_{2A}$ Adenosine receptors agonists for pig brain striatum $A_{2A}$ receptors and the reversal time ($t_{0.9}$) of coronary vasodilation in pig heart Table 2).

TABLE 5

Reversal time of coronary vasodilation by adenosine and
adenosine receptor agonists in rate isolated perfused

| Agonist | $t_{0.5}$ (min) | $t_{0.9}$ (min) | n |
|---|---|---|---|
| R-PIA | 7.9 ± 0.1 | 12.6 ± 0.8 | 3 |
| CGS21680 | 14.5 ± 0.5 | 19.5 ± 09 | 3 |
| CVT-2995 | 17.5 ± 1.2 | 23.2 ± 2.1 | 4 |
| WRC0470 | 21.9 ± 0.9 | 27.9 = 1.4 | 6 |
| CVT-3032 | 4.1 ± 0.3 | 9.8 ± 1.4 | 4 |
| CVT-3033 | 3.4 ± 0.5 | 8.4 ± 2.2 | 4 |
| CVT-3146 | 5.2 ± 0.2 | 11.3 ± 1.1 | 5 |
| YT-146 | 17.7 ± 1.0 | 25.8 ± 4.0 | 3 |
| CVT-3003 | 3.4 ± 0.1 | 9.2 ± 2.2 | 4 |
| CVT-3006 | 16.1 ± 0.1 | 21.8 ± 2.0 | 3 |
| CVT-3100 | 5.1 ± 0.6 | 10.1 ± 0.2 | 4 |
| CVT-3101 | 16.7 ± 0.5 | 25.6 ± 0.3 | 3 |
| CVT-3126 | 8.3 ± 0.4 | 12.6 ± 0.3 | 4 |
| CVT-3127 | 14.8 ± 2.1 | 15.0 ± 0.8 | 3 |
| CVT-3141 | 14.4 ± 1.9 | 21.3 ± 3.9 | 4 |
| CVT-3144 | 13.6 ± 1.3 | 18.4 ± 1.9 | 4 |
| HENECA | 28.6 ± 1.1 | 32.8 ± 3.1 | 3 |
| Adenosine | 1.6 ± 0.1 | 5.6 ± 0.8 | 11 |

Times (in minutes) to 50% and 90% ($t_{0.5}$ and $t_{0.9}$, respectively) reversal of the increases in coronary conductance caused by adenosine and adenosine receptor agonists.
Values are the mean ± SEM of single determination in each of n preparation.

TABLE 6

Magnitude and reversal time of coronary dilation caused by various
adenosine receptor agonists in open-chest anesthetized pigs

| Agonist | Dose | CBF (fold-increas) | $t_{0.5}$ (min) | $t_{0.9}$ (min) | n |
|---|---|---|---|---|---|
| CVT-3146 | 10 ug/kg/min | 3.40 ± 0.04 | 1.9 ± 0.2 | 10.1 ± 0.7 | 3 |
| CVT-3146 | 30 ug/kg/min | 3.38 ± 0.39 | 2.6 ± 0.5 | 12.3 ± 1.1 | 6 |
| CVT-3032 | 30 ug/kg/min | 3.78 ± 0.70 | 2.3 ± 0.6 | 9.6 ± 1.0 | 3 |
| CVT-3033 | 50 ug/kg/min | 3.33 ± 0.58 | 3.1 ± 0.9 | 12.0 ± 1.0 | 3 |
| WRC0470 | 1 ug/kg/min | 3.14 ± 0.24 | 9.5 ± 0.8 | 22.5 ± 1.6 | 6 |
| CGS21680 | 2 ug/kg/min | 3.54 ± 0.09 | 9.7 ± 0.8 | 21.4 ± 0.8 | 3 |
| YT-146 | 1 ug/kg/min | 3.44 ± 0.47 | 17.8 ± 3.4 | 32.9 ± 5.6 | 3 |

Maximal "fold-increase" and time (in minutes) to 50% and 90% ($t_{0.5}$ and $t_{0.9}$, respectively) reversal of the increases in coronary blood flow caused by various adenosine receptor agonists.
Data represent mean ± SEM of one or two measurements in each of n pigs.

Example 6

The following example demonstrate the effects of CVT-3146 on the hemodynamic parameters in dogs.

Ten mongrel dogs (weighing 23-27 kg) were premedicated with Acepromazine (0.3 mg/kg im) and anesthetized with sodium pentobarbital (25 mg/kg) and then intubated and ventilated with room air. A thoracotomy was performed in the left fifth intercostal space using sterile surgical techniques. A Tygon catheter (Cardiovascular Instruments, Inc.) was placed in. the descending thoracic aorta for the measurements of blood pressure. A solid-state pressure gauge (P6.5, Konisberg Instrument, Inc) was placed in the apex of the left ventricle for the measurement of the left ventricular systolic pressure (LVSP) and calculation of first
derivative of left ventricular pressure (LV dP/dt). A Doppler transducer (Craig Hartley) was placed on the left circumflex coronary artery for measurement of CBF. An hydraulic coronary occluder (In Vivo Metric, Inc) was implanted in 4 dogs around the left circumflex coronary artery. The chest was closed in layers and the catheters and wires were run subcutaneously and exited in the interscapular area. The dogs were allowed 10 to 14 days to recover fully
from the surgery and were trained to lie on a laboratory table.

The protocols were approved by the Institutional Animal Care and Use Committee of New York Medical College and conform to the "Guiding Principles for the use and Care of Laboratory Animals" of the National Institute of Health and the American Physiology Society.

Arterial pressure was measured by connecting the previously implanted catheter to a strain-gauge transducer (P23ID, Statham) and mean arterial pressure (MAP) was derived using 2-Hz low-pass filter. LV pressure was measured from the solid-state pressure gauge, and LV dP/dt was calculated using a microprocessor set as a differentiator and having a frequency response flat to 700 Hz (LM 324, National Semiconductor). Left circumflex CBF was measured using a pulsed Doppler flowmeter (System 6, Triton technology), and mean CBF was derived using a 2-Hz low-pass filter. Mean CR was calculated as the quotient of MAP and CBF. Heart rate was monitored from the pressure pulse interval using a cardiotachometer (Beckman Instruments). The lead-2 of the electrocardiogram was recorded during the experiments in order to examine the alterations in the AV nodal conduction (PR interval). All signals were recorded on a direct-writing oscillograph (Gould 2800).

To determine the effects of adenosine and CVT 3146 on CBF and CR in resting dogs baseline hemodynamics and CBF were recorded and then, increasing doses of adenosine: 13, 27, 67, 134 and 267 μg/kg and CVT-3146: 0.1, 0.175, 0.25, 0.5, 1.0, 2.5, 5 μg/kg in 10 ml volumes were administered iv for 10 minutes in 10 ml via a catheter inserted into a peripheral vein. Hemodynamics were measured before, during and after each dose. Following each dose hemodynamics were allowed to return to baseline before the administration of the next dose. Changes in heart rate, blood pressure, CBF, and ECG were recorded.

The duration of coronary vasodilation was determined using two different injection protocols: 1) an iv infusion of 10 ml in 10 seconds and; 2) iv infusion of 10 ml in 30 seconds. The time to the peak effect in mean CBF increase and the duration during which CBF remained at least 2 fold above baseline.

To determine whether tachyphylaxis occurred, three consecutive injections of 1 μg/kg CVT-3146 were given as intravenous injections (10 ml in 30 seconds) via a catheter inserted into a peripheral vein. The hemodynamics were allowed to return to baseline between doses. Hemodynamics were measured before, during and after each dose.

Hemodynamic results are expressed as mean±SEM. Data were analyzed using one way repeated measures analysis of variance, with Student-Neuman-Keuls post hoc analysis to identify which means were significantly (p<0.05) different (Sigma Stat, Version 2.2, Jandel Scientific, San Rafael, Calif.). To determine the agonist potency from dose-response curves, doses producing 50% of maximum effect ($ED_{50}$) were calculated by fitting curves using the Boltzmann equation. $ED_{50}$ were compared using a Student's t-test (p<0.05 being considered as significant). Because no statistical differences were found among the baseline values between each dose for each parameter measure, the first baseline registered during each experiment was used as the control value. A Student's t-test was used to compare the changes in CBF and hemodynamic parameters produced by 2.5 m/kg CVT-3146, 267 μg/kg adenosine and 25 μg/kg nitroglycerin (p<0.05 being considered significant).

Figure 11:
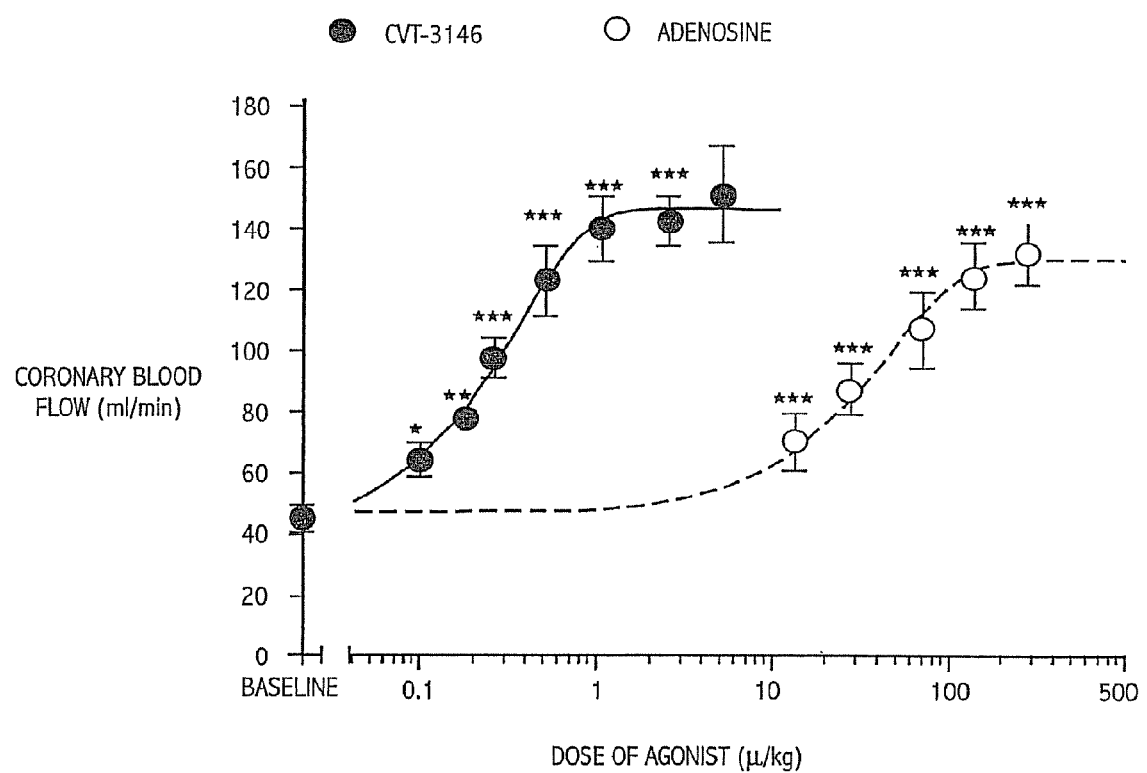
FIG. 11. Increases in CBF caused by CVT-3146 and adenosine in conscious dogs. Each data point is mean±SEM of the peak effect in CBF from 6 dogs. *: p<0.05, †: p<0.01 and ‡: p<0.001. Adenosine: (O) and CVT-3146 (O).

A dose-response curve of the effect of CVT-3146 on CBF is shown in FIG. 11. An IV bolus injection of CVT-3146 caused a dose-dependent increase in mean CBF, with a $ED_{50}$ of 0.34±0.08 μg/kg and a maximal increase of 154±16 ml/min from baseline (45±3 ml/min) In comparison to CVT-3146, adenosine was less potent having an $ED_{50}=51\pm15$ µg/kg (p<0.05). The maximal increase in mean CBF stimulated by CVT-3146 and adenosine were similar.

CVT-3146 produced a maximal decrease in CR of 73±2% and 75±2% at 2.5 µg/kg at 5 µg/kg, respectively. Adenosine produced a maximal decrease of 73±1% at 267 µg/kg (data not shown).

The effects of CVT-3146 and adenosine on left ventricular systolic pressure and dP/dt were compared. Increasing doses of CVT-3146 did not cause significant changes in LVSP (data not shown). In comparison, adenosine increased LVSP at 67 µg/kg, 134 µg/kg and 267 µg/kg, by 12±3%, 12±3% and 18±6%, respectively. Both adenosine (267 µg/kg) and CVT-53146 (2.5 µg/kg) increased the dP/dt by 29±17% and 39±7% respectively.

Example 7

Example 7 demonstrates the differential effects of CVT-3146 on blood flow velocity in coronary and peripheral arteries, systemic arterial blood pressure and heart rate in anesthetized dogs.

Mongrel dogs (either sex, 17-21 kg; n=6) were obtained from a local vendor (Barton, Oxford, N.J.). Blood flow velocity in the coronary and cranial circumflex arteries was measured using Doppler transducer-tipped guide wires 0.014" in diameter (FloWire®, model 1400J) purchased from Cardiometrics, Inc., Mountain View, Calif. For the positioning of the FloWire, a Judkins left coronary guiding catheter (JL3.5, 8F; Cordis) was used. Vascular arterial angiography was performed using Hypaque-76 contrast fluid (Bracco Diagnostics, Inc., Princeton, N.J.; Lot #9H28899) and a mobile fluoroscopic unit (Philips, BV 29). Systemic arterial blood pressure was measured using an electronic transducer-tipped catheter (Millar). The following pharmacological agents were used: CVT-3146 (CV Therapeutics; Lot #315-53), heparin (Solopak Laboratories, Inc., Elk Grove Village, Ill.; Lot #960211) and sodium pentobarbital (lot #9700), and acepromazine (lot #3960960), obtained from JA Webster (Fort Dodge, Iowa).

Dogs were sedated with acepromazine (0.25 mg/kg), anesthetized with sodium pentobarbital (30 mg/kg+additional doses (1 mg/kg) given as necessary to maintain the level of anesthesia), intubated with endrotracheal tube and artificially ventilated with room air using a respirator. Following the administration of heparin (20 U/kg+100 U/hr), the pressure transducer-tipped catheter was introduced through the left femoral artery and positioned in the descending aorta. The Doppler FloWire was introduced through the right femoral artery. A peripheral vein was cannulated for the administration of all drugs. Doses of 1 µg/kg of CVT-3146 and 300 or 200 µg/kg adenosine (Adenosine) were given multiple times, once or twice when the Doppler catheter was positioned in a coronary artery and again when the catheter was positioned in the cranial circumflex humeral artery. The sequence of positioning of the Doppler catheter was reversed in consecutive experiments. In each dog, baseline values of measured parameters were recorded following a stabilization period of 20 minutes, and CVT-3146 and Adenosine were given as intravenous bolus injections (<0.5 ml) followed by a physiologic saline solution flush (10 ml); the time required for both injections of each drug was <15 sec. All parameters were allowed to recover (>30 min) to their respective baseline values between two consecutive drug administrations. In all six dogs studied, the effect of CVT-3146 on coronary artery APV was determined. The effect of CVT-3146 on peripheral artery APV was determined in five of the six dogs. The effect of adenosine on both coronary and peripheral artery APV was studied in five of the six dogs.

Systemic arterial blood pressure (BP) and electrocardiograms (ECG) were monitored and recorded using Gould Data Acquisition System (model 13-4615-65A), a video cassette recorder (Teac, XR 5000) and a chart recorder (Astromed, 9600). The following parameters were monitored and recorded: Average peak coronary and peripheral artery blood flow velocity (APV), mean arterial blood pressure (MAP) (mmHg), and sinus cycle length (SCL; msec). Differences in measure parameters were tested for statistical significance using ANOVA and Student's t test corrected for multiple measurements. Data are expressed as the mean±SEM.

CVT-3146 increased APV in the coronary vasculature by 2.6±0.2-fold while its increase of APV in the peripheral arteries was only 1.1±0.1-fold (Table 7). In contrast the vasodilatory action of adenosine was similar in the two vascular beds: specifically, adenosine increased APV in the coronary vasculature by 2.5+0.3-fold while its increase of APV in the peripheral arteries was 2.0±0.4-fold.

TABLE 7

Magnitude of Increases in Coronary and Peripheral Blood Flow Velocity of CVT-3146 and Adenosine in Anesthetized Close-chest Dogs

| Agonist | Coronary | N | 'Peripheral | N |
| --- | --- | --- | --- | --- |
| CVT-3146 | 2.6 ± 0.2 | 6 | 1.1 ± 0.1 | 5 |
| Adenosine | 2.5 ± 0.3 | 5 | 2.0 ± 0.4 | 5 |

Data are the maximal "folds increase" in average peak velocity (APV) above baseline ($APV_{max}/APV_{baseline}$) after intravenous injection of CVT-3146 (1 µg/kg) and adenosine (200 or 300 µg/kg)

Figure 12A:
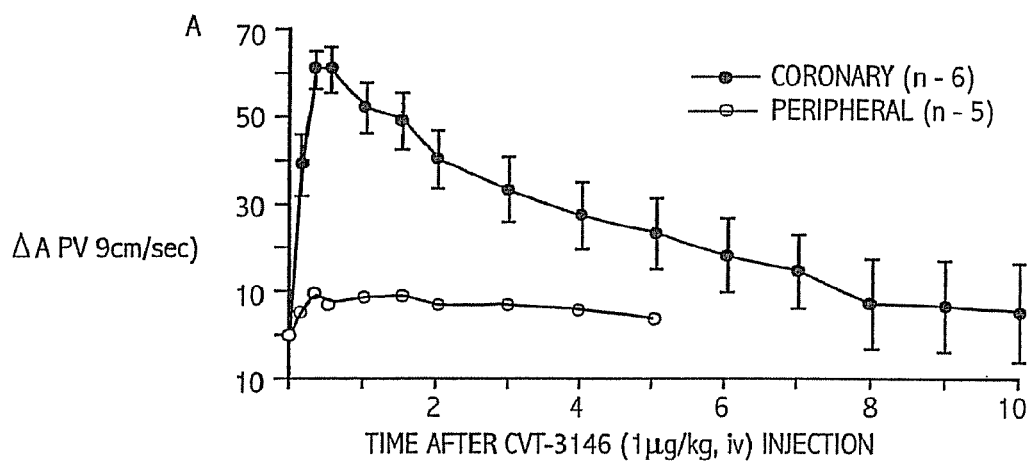
FIG. 12A and FIG. 12B. Time course of changes in average peak coronary (O) and peripheral (O) artery blood flow velocity after an IV bolus injection of CVT-3146 (μg/kg) (A) and adenosine (200-300 μg/kg)(B). Each point represents the changes in average peak flow velocity (ΔAPV) in comparison with the baseline values and represents the mean±SEM of single determinations.
Figure 12B:
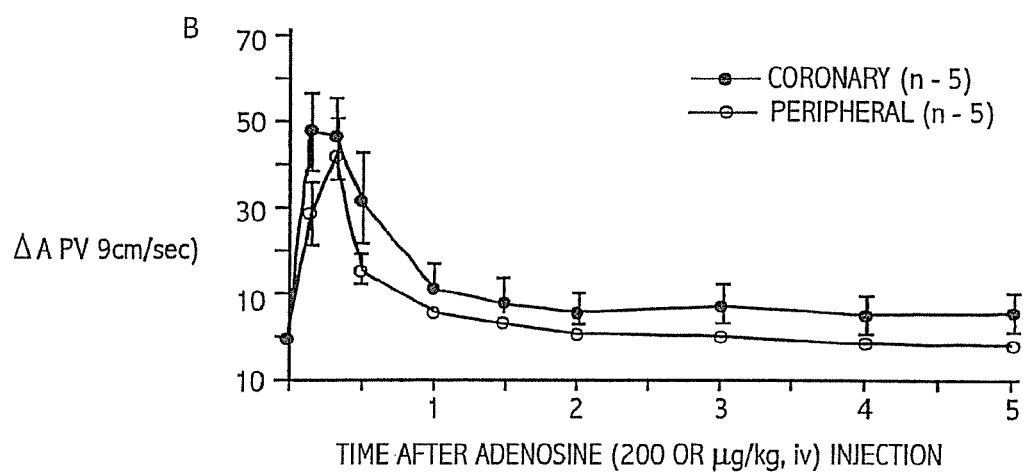

The time course of the changes in CBF, PBF, HR and MAP and heart rate caused by CVT-3146 and adenosine are depicted in FIG. 12A and FIG. 12B and summarized in Table 8. The duration of >2-fold increase in coronary APV caused by CVT-3146 and adenosine was <120 sec and <20 sec, respectively; all parameters returned to baseline within 10 min and 5 min post injection of adenosine and CVT-3146, respectively. Based on the differential selectivity of the vasodilatory effects of CVT-3146 and adenosine in the coronary and the peripheral arteries, and the dosage used, CVT-3146 is approximately 600 times more selective than adenosine in vasodilating the coronary vs. the peripheral arterial vasculature.

TABLE 8

Differential effects of CVT-3146 and Ado on blood flow velocity, heart rate and mean arterial blood pressure (MAP)

| | CVT-3146 (1 ug/kg) | | | | | | Ado (200 or 300 ug/kg) | | | | | |
| --- | --- | --- | --- | --- | --- | --- | --- | --- | --- | --- | --- | --- |
| | Coronary (n = 6) | | | Peripheral (n = 5) | | | Coronary (n = 5) | | | Peripheral (n = 5) | | |
| Time | HR | MAP | APV | HR | MAP | APV | HR | MAP | APV | HR | MAP | APV |
| Baseline | 171 ± 8 | 128 ± 7 | 49 ± 7 | 162 ± 9 | 116 ± 8 | 34 ± 8 | 170 ± 10 | 126 ± 6 | 42 ± 5 | 165 ± 10 | 118 ± 8 | 33 ± 3 |
| 10" | 177 ± 8 | 126 ± 9 | 84 ± 4 | 167 ± 6 | 114 ± 9 | 34 ± 4 | 174 ± 7 | 126 ± 8 | 90 ± 10 | 171 ± 6 | 107 ± 9 | 62 ± 9 |

TABLE 8-continued

Differential effects of CVT-3146 and Ado on blood flow velocity, heart rate and mean arterial blood pressure (MAP)

| | CVT-3146 (1 ug/kg) | | | | | | Ado (200 or 300 ug/kg) | | | | | |
|---|---|---|---|---|---|---|---|---|---|---|---|---|
| | Coronary (n = 6) | | | Peripheral (n = 5) | | | Coronary (n = 5) | | | Peripheral (n = 5) | | |
| Time | HR | MAP | APV | HR | MAP | APV | HR | MAP | APV | HR | MAP | APV |
| 20" | 186 ± 9 | 116 ± 9 | 106 ± 8 | 177 ± 7 | 107 ± 8 | 38 ± 4 | 166 ± 11 | 90 ± 9 | 85 ± 10 | 162 ± 15 | 85 ± 9 | 76 ± 10 |
| 30" | 188 ± 7 | 117 ± 7 | 109 ± 10 | 183 ± 8 | 111 ± 6 | 41 ± 4 | 173 ± 6 | 107 ± 9 | 75 ± 9 | 168 ± 9 | 87 ± 9 | 59 ± 11 |
| 1' | 186 ± 7 | 112 ± 7 | 100 ± 12 | 182 ± 7 | 102 ± 6 | 42 ± 4 | 175 ± 5 | 113 ± 6 | 39 ± 8 | 171 ± 6 | 105 ± 6 | 44 ± 7 |
| 1.5' | 186 ± 7 | 110 ± 7 | 97 ± 11 | 184 ± 7 | 99 ± 7 | 42 ± 4 | 171 ± 5 | 117 ± 6 | 55 ± 8 | 171 ± 6 | 106 ± 7 | 38 ± 4 |
| 2' | 185 ± 7 | 110 ± 7 | 88 ± 11 | 187 ± 8 | 98 ± 7 | 40 ± 4 | 170 ± 5 | 120 ± 6 | 52 ± 7 | 169 ± 6 | 110 ± 6 | 35 ± 3 |
| 3' | 185 ± 7 | 110 ± 6 | 81 ± 11 | 187 ± 8 | 97 ± 7 | 40 ± 4 | 168 ± 8 | 125 ± 6 | 49 ± 6 | 165 ± 9 | 115 ± 7 | 33 ± 3 |
| 4' | 183 ± 8 | 110 ± 6 | 75 ± 11 | 186 ± 8 | 100 ± 6 | 39 ± 4 | 164 ± 10 | 126 ± 6 | 47 ± 6 | 160 ± 9 | 119 ± 8 | 31 ± 3 |
| 5' | 183 ± 8 | 112 ± 6 | 72 ± 11 | 185 ± 8 | 101 ± 6 | 37 ± 5 | 163 ± 10 | 128 ± 6 | 47 ± 6 | 158 ± 10 | 121 ± 7 | 30 ± 2 |
| 6' | 182 ± 8 | 113 ± 6 | 65 ± 11 | | | | | | | | | |
| 7' | 181 ± 8 | 115 ± 6 | 63 ± 12 | | | | | | | | | |
| 8' | 180 ± 8 | 117 ± 6 | 55 ± 11 | | | | | | | | | |
| 9' | 177 ± 9 | 119 ± 6 | 55 ± 11 | | | | | | | | | |
| 10' | 176 ± 9 | 120 ± 6 | 53 ± 11 | | | | | | | | | |

Values are the mean ± SEM of single determinations in each of the preparations (n).

We claim:

1. A method for increasing coronary blood flow in a mammal in need thereof comprising administering a pharmaceutically effective amount of a compound that is

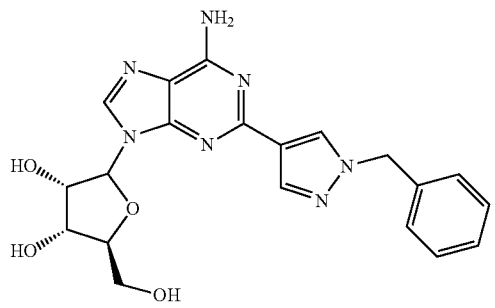 [SMILES: Nc1nc(-c2cnn(Cc3ccccc3)c2)nc2c1ncn2C1O[C@@H](CO)[C@H](O)[C@@H]1O]

wherein the pharmaceutically effective amount is about 0.3 to 103 µg/kg, and wherein the administration causes an increase in peripheral blood flow that is less than 50% of the increase in coronary blood flow.

2. The method of claim 1, wherein the dose of the compound is 30 µg/kg.

3. The method of claim 1, wherein the step of administering the pharmaceutically effective amount of the compound takes place by infusion of a pharmaceutically acceptable composition thereof.

4. The method of claim 1, wherein the step of administering the pharmaceutically effective amount of the compound takes place by a bolus injection of a pharmaceutically acceptable composition thereof.

5. A method of myocardial perfusion imaging in a human in need thereof comprising: administering to the human (a) a dose of a compound

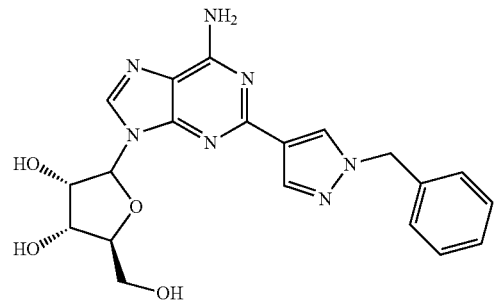 [SMILES: Nc1nc(-c2cnn(Cc3ccccc3)c2)nc2c1ncn2C1O[C@@H](CO)[C@H](O)[C@@H]1O]

wherein the dose is about 0.3 to 103 µg/kg and (b) a radionuclide, and thereafter determining areas of insufficient blood flow.

* * * * *

UNITED STATES PATENT AND TRADEMARK OFFICE
CERTIFICATE OF CORRECTION

| | |
|---|---|
| PATENT NO. | : 9,163,057 B2 |
| APPLICATION NO. | : 14/014169 |
| DATED | : October 20, 2015 |
| INVENTOR(S) | : Luiz Belardinelli et al. |

It is certified that error appears in the above-identified patent and that said Letters Patent is hereby corrected as shown below:

ON THE TITLE PAGE, ITEM [63], RELATED U.S. APPLICATION DATA:

For application No. 10/614,702, please replace "Mar. 7, 2003" with --Jul. 3, 2003--.

Signed and Sealed this
Twenty-ninth Day of March, 2016

Michelle K. Lee
*Director of the United States Patent and Trademark Office*